US011116765B2

(12) United States Patent
Gonda et al.

(10) Patent No.: US 11,116,765 B2
(45) Date of Patent: Sep. 14, 2021

(54) LIPOSOMAL CIPROFLOXACIN FORMULATIONS WITH ACTIVITY AGAINST NON-TUBERCULOUS MYCOBACTERIA

(71) Applicant: GRIFOLS, S.A., Los Angeles, CA (US)

(72) Inventors: Igor Gonda, San Francisco, CA (US); James Blanchard, El Granada, CA (US); David C. Cipolla, San Ramon, CA (US); Luiz Eduardo Moreira Bermudez, Corvallis, OR (US)

(73) Assignee: GRIFOLS, S.A., Los Angeles, CA (US)

( * ) Notice: Subject to any disclaimer, the term of this patent is extended or adjusted under 35 U.S.C. 154(b) by 0 days.

(21) Appl. No.: 16/914,122

(22) Filed: Jun. 26, 2020

(65) Prior Publication Data

US 2020/0323845 A1 Oct. 15, 2020

Related U.S. Application Data

(60) Continuation of application No. 16/506,675, filed on Jul. 9, 2019, now abandoned, which is a continuation
(Continued)

(51) Int. Cl.
*A61K 31/496* (2006.01)
*A61K 9/127* (2006.01)
(Continued)

(52) U.S. Cl.
CPC .......... *A61K 31/496* (2013.01); *A61K 9/0078* (2013.01); *A61K 9/12* (2013.01);
(Continued)

(58) Field of Classification Search
CPC ..................................................... A61K 31/496
See application file for complete search history.

(56) References Cited

U.S. PATENT DOCUMENTS 5,580,575 A 12/1996 Unger et al.
5,902,604 A 5/1999 Lou et al.
(Continued)

FOREIGN PATENT DOCUMENTS

CA 2215716 C 12/1999
CA 2896083 A1 6/2007
(Continued)

OTHER PUBLICATIONS

Anonymous: "Nanotechnology for Cancer Therapy" CRC Press XP-002772115 (Dec. 19, 2006) 1 page.
(Continued)

*Primary Examiner* — Benjamin J Packard
(74) *Attorney, Agent, or Firm* — Barnes & Thornburg LLP; Ryan P. Cox

(57) ABSTRACT

Methods of treatment of NTM lung infections using formulations of liposomal ciprofloxacin. Specific liposome formulations and delivery of such for treatment of respiratory tract infections and other medical conditions, and devices and formulations used in connection with such are described.

15 Claims, 1 Drawing Sheet

Related U.S. Application Data of application No. 15/821,193, filed on Nov. 22, 2017, now Pat. No. 10,376,508, which is a continuation of application No. 15/362,405, filed on Nov. 28, 2016, now Pat. No. 9,844,548, which is a division of application No. 14/675,218, filed on Mar. 31, 2015, now Pat. No. 9,532,986.

(60) Provisional application No. 61/976,727, filed on Apr. 8, 2014.

(51) Int. Cl.
    A61K 9/00    (2006.01)
    A61K 9/12    (2006.01)
    A61K 45/06    (2006.01)

(52) U.S. Cl.
    CPC ............. *A61K 9/127* (2013.01); *A61K 45/06* (2013.01); *A61K 9/0073* (2013.01); *Y02A 50/30* (2018.01)

(56) References Cited

U.S. PATENT DOCUMENTS

| | | |
|---|---|---|
| 5,939,096 A | 8/1999 | Clerc et al. |
| 7,244,413 B2 | 7/2007 | Barbera-Guillem |
| 8,071,127 B2 | 12/2011 | Cipolla et al. |
| 8,119,156 B2 | 2/2012 | Cipolla et al. |
| 8,226,975 B2 | 7/2012 | Weers |
| 8,268,347 B1 | 9/2012 | Cipolla et al. |
| 8,414,915 B2 | 4/2013 | Cipolla et al. |
| 8,642,075 B2 | 2/2014 | Weers |
| 8,673,348 B2 | 3/2014 | Weers |
| 8,673,349 B2 | 3/2014 | Weers |
| 2002/0132814 A1 | 9/2002 | Oethinger et al. |
| 2002/0102293 A1 | 11/2002 | Sachse et al. |
| 2004/0091541 A1 | 5/2004 | Unger |
| 2004/0142026 A1 | 7/2004 | Boni et al. |
| 2005/0214224 A1 | 9/2005 | Weers et al. |
| 2006/0110441 A1 | 5/2006 | Wong et al. |
| 2006/0159739 A1 | 7/2006 | Lasic et al. |
| 2006/0280691 A1 | 12/2006 | Wang et al. |
| 2007/0031344 A1 | 2/2007 | Osbakken et al. |
| 2007/0196461 A1 | 8/2007 | Weers |
| 2009/0196917 A1 | 8/2009 | Joguparthi et al. |
| 2009/0269396 A1* | 10/2009 | Cipolla ............... A61K 9/0073 424/450 |
| 2010/0260829 A1 | 10/2010 | Boni et al. |
| 2012/0009253 A1 | 1/2012 | Fleischer et al. |
| 2013/0028960 A1 | 1/2013 | Weers |
| 2013/0039847 A1 | 2/2013 | Gessler et al. |
| 2013/0052260 A1 | 2/2013 | Weers |
| 2013/0064883 A1 | 3/2013 | Weers |
| 2013/0071469 A1 | 3/2013 | Weers |
| 2013/0087480 A1 | 4/2013 | Stark et al. |
| 2013/0121918 A1 | 5/2013 | Hong et al. |
| 2013/0330440 A1 | 12/2013 | Fulgham |
| 2014/0072620 A1 | 3/2014 | Weers |
| 2014/0161876 A1 | 6/2014 | Isoda |
| 2014/0255472 A1 | 9/2014 | Geall et al. |
| 2015/0110855 A1 | 4/2015 | Cipolla et al. |
| 2015/0283076 A1 | 10/2015 | Cipolla et al. |
| 2015/0283133 A1 | 10/2015 | Gonda et al. |

FOREIGN PATENT DOCUMENTS

| | | |
|---|---|---|
| CN | 101553209 A | 10/2009 |
| CN | 102309448 B | 7/2014 |
| JP | 11507369 A | 6/1999 |
| JP | 2003504389 A | 2/2003 |
| JP | 2010507658 A | 3/2010 |
| WO | 1996039121 A1 | 12/1996 |
| WO | 200105372 A2 | 1/2001 |
| WO | 2008063341 A2 | 5/2008 |
| WO | 2014052634 A1 | 4/2014 |

OTHER PUBLICATIONS

Ausborn et al., "The protective effect of free and membrane-bound cryoprotectants during freezing and freeze-drying of liposomes" Journal of Controlled Release (1994) 30:105-116.
Bangham, et al., "Diffusion of Univalent Ions across the Lamellae of Swollen Phospholipids" J. Mol. Niol., 13:238-252 (1965).
Bruinenberg P., et al., "Safety, tolerability and pharmacokinetics of novel liposomal ciprofloxacin formulations for inhalation in healthy volunteers and in non-cystic bronchiectasis patients" Am. J. Respir. Crit. Care Med. 181;2010: A3192 / www.atsjournals.org.
Carter G., et al., "Characterization of biofilm formation by clinical isolates of *Mycobacterium avium*", Journal of Medical Microbiology (2003) 52:747-52.
Cipolla D., et al., "Liposomal Formulations for Inhalation", Ther. Deliv., (2013) 4(8)1047-1072. doi: 10.4155/tde.13.71.
Cipolla D., et al., "Development and Characterization of an In Vitro Release Assay for Liposomal Ciprofloxacin for Inhalation", J. Pharm. Sci., (2014) 103:314-327. doi: 10.1002/ios.23795.
Cipolla, et al., "Formation of drug nanocrystals under nanoconfinement afforded by liposomes," RSC Adv. (Jan. 2016) 6:6223-6233.
Conley, et al., "Aerosol Delivery of Liposome-Encapsulated Ciprofloxacin: Aerosol Characterization and Efficacy against Francisella tularensis Infection in Mice" Antimicrobial Aaents 41(6): 1288-1292 (Jun. 1997).
Costa, et al., "Freeze-Anneal-Thaw Cycling of Unilamellar Liposomes: Effect on Encapsulation Efficiency" Pharm. Res. (2014) 31:97-103.
Koh, et al., "Clinical Significance of Differentiation of *Mycobacterium massiliense* from *Mycobacterium abscessus*" American Journal of Respiratory and Critical Care Medicine (2011) 183:405-410.
Kokyu (Respiration) (2013) 32(7):619-623.
Kurashima, "*Mycobacterium abscessas*" Igaku no Ayumi (Progress in Medicine) (Mar. 8, 2014) 248(10):792-798.
Lasic, et al., "Gelation of liposome interior: A novel method for drug encapsulation" FEBS Lett., (1992) 312:255-258.
Lasic et al., "Transmembrane gradient drive phase transitions within vesicles: lessons for drug delivery" Biochimica et Biophysica Acta (1995) 1239:145-156.
Majumdar et al., Efficacies of liposome-encapsulated streptomycin and ciprofloxacin against *Mycobacterium avium*—N. intracellulare complex infections in human peripheral blood monocvtes/macroohaaes. Antimicrob Aaents Chemother (1992) 36:2808-15.
Maurer et al., "Anomalous solubility behavior of the antibiotic ciprofloxacin encapsulated in liposomes: a 1H-NMR study." Biochimica et Biophysica Acta (1998) 1374:9-20.
Piersimoni et al., "Pulmonary infections associated with non-tuberculous mycobacteria in immunocompetent patients" Lancet Infect. Dis. (2008) 8:323-334.
Smith, et al., "Safety of Aerosol Tobramycin administration for 3 months to patients with cystic fibrosis." Ped. Pulmonol. (1989); 7(4):265-271.
Stark, et al., "Long-term stability of sterically stabilized liposomes by freezing and freeze-drying: Effects of cryoprotectants on structure", Eur. J. Pharm. Sci. 41(2010) 546-555.
Strauss, et al., "Stabilization of lipid bilayer vesicles by sucrose during freezing", Proc. Natl. Acad. Sci. USA (1986) 83:2422-2426.
Van Heeckeren, et al., "Effect of Pseudomonas infection on weight loss, lung mechanics, and cytokines in mice." Am J Respir Grit Care Med. (Jan. 2000); 161(1):271.
Van Heeckeren, et al., "Murine Models of chronic Pseudomonas aeruginosa lung infection" Lab Anim (Jul. 2002}; 36(3):291-312.
Webb, et al., "Antibacterial Efficacy against an In Vivo *Salmonella typhimurium* Infection Model and Pharmacokinetics of a Liposomal Ciprofloxacin Formulation", Antimicrobial Agents and Chemotherapy (Jan. 1998) 42(1):45-52.
Weber A, et al., "Nebulizer delivery of tobramycin to the lower respiratory tract". Pediatr Pulmonol. (May 1994}; 17 (5):331-9.
Wolkers, et al.,"Preservation of dried liposomes in the presence of sugar and phosphate", Biochim. Biphys. Acta. (2004) 1661:125-134.

(56) References Cited

OTHER PUBLICATIONS

Wong, et al., "Liposome delivery of ciprofloxacin against intracellular Francisella tularensis infection" Journal of Controlled Release, 92; 265-273 (2003}.

Yamazaki, et al., “The ability to form biofilm influences *Mycobacterium avium* invasion and translocation of bronchial epithelial cells”, Cellular Microbiology (2006) 8(5):806-14.

Zhigaltsev, et al., “Formation of drug-arylsulfonate complexes inside liposomes: A novel approach to improve drug retention”, J. Control Rel. 110 (2006): 378-386.

* cited by examiner

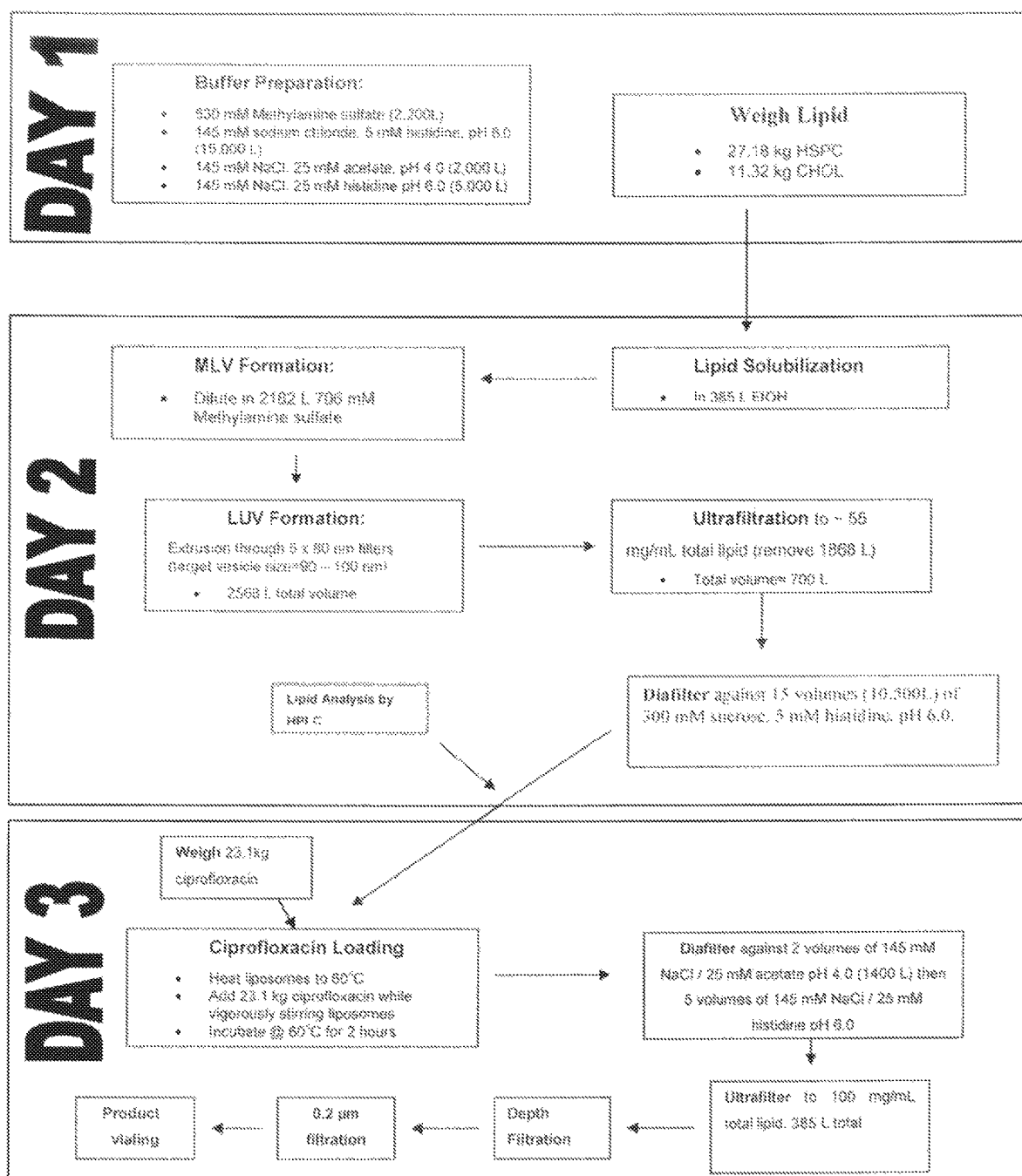

LIPOSOMAL CIPROFLOXACIN FORMULATIONS WITH ACTIVITY AGAINST NON-TUBERCULOUS MYCOBACTERIA

RELATED APPLICATIONS

This application is a continuation of U.S. application Ser. No. 16/506,675, filed Jul. 9, 2019, which is a continuation of U.S. patent application Ser. No. 15/821,193, filed Nov. 22, 2017, and issued as U.S. Pat. No. 10,376,508 on Aug. 13, 2019; which is a continuation of U.S. patent application Ser. No. 15/362,405, and issued and U.S. Pat. No. 9,844,548, on Dec. 19, 2017; which is a division of U.S. patent application Ser. No. 14/675,218, filed Mar. 31, 2015, and issued as U.S. Pat. No. 9,532,986, on Jan. 3, 2017; which claims priority to U.S. Provisional Patent Application No. 61/976,727, filed Apr. 8, 2014, the disclosures of each of which are hereby incorporated by reference in their entirety.

GOVERNMENT RIGHTS

This invention was made with government support Small Business Innovation Research Grant 1R43-AI-106188-01 awarded by National Institutes of Allergy and Infectious Disease, National Institutes of Health. The government has certain rights in this invention.

FIELD OF THE INVENTION

The present invention relates to pharmaceutical compositions of liposomal ciprofloxacin for inhalation to prevent or treat respiratory tract infections caused by a variety of microorganisms or intracellular pathogens, particularly non tuberculous mycobacteria (NTM).

BACKGROUND OF THE INVENTION

Respiratory tract infections are caused by a variety of microorganisms. Infections which are persistent have a myriad of consequences for the health care community including increased treatment burden and cost, and for the patient in terms of more invasive treatment paradigms and potential for serious illness or even death. It would be beneficial if an improved treatment paradigm were available to provide prophylactic treatment to prevent susceptible patients from acquiring respiratory tract infections as well as increasing the rate or effectiveness of eradication for patients already infected with the microorganisms.

Pulmonary infections with non-tuberculosis mycobacteria (NTM) are notoriously difficult to treat. They exist in the lungs in various forms, including within macrophages and in biofilms. These locations are particularly difficult to access with antibiotics. Furthermore, the NTM may be either in a dormant (termed sessile), or a replicating phase, and an effective antibiotic treatment would target both phases. We have found, surprisingly, that certain compositions of ciprofloxacin that include ciprofloxacin encapsulated in liposomes are effective in their antibacterial activity both against NTM harbored in macrophages as well as NTM that exist dormant in biofilms.

Lung infection from *Mycobacterium avium* subspecies hominissuis (hereafter referred as *M. avium*) and *Mycobacterium abscessus* (hereafter referred to as *M. abscessus*) is a significant health care issue and there are major limitations with current therapies. The incidence of pulmonary infections by NTM is increasing (Adjemian et al., 2012; Prevots et al, 2010), specifically with *M. avium* and *M. abscessus* (Inderlied et al, 1993). About 80% of NTM in US is associated with *M. avium* (Adjemian et al., 2012; Prevots et al, 2010). *M. abscessus*, which is amongst the most virulent types, ranks second in incidence (Prevots et al, 2010). Diseases caused by both mycobacteria are common in patients with chronic lung conditions, e.g., emphysema, cystic fibrosis, and bronchiectasis (Yeager and Raleigh, 1973). They may also give rise to severe respiratory diseases, e.g., bronchiectasis (Fowler et al, 2006). The infections are from environmental sources and cause progressive compromising of the lung. Current therapy often fails on efficacy or is associated with significant side-effects. *M. avium* infection is usually treated with systemic therapy with a macrolide (clarithromycin) or an azalide (azithromycin) in combination with ethambutol and amikacin. Oral or IV quinolones, such as ciprofloxacin and moxifloxacin, can be used in association with other compounds (Yeager and Raleigh, 1973), but higher intracellular drug levels need to be achieved for maximal efficacy. Oral ciprofloxacin has clinical efficacy against *M. avium* only when administered in combination with a macrolide or an aminoglycoside (Shafran et al 1996; de Lalla et al, 1992, Chiu et al, 1990). Studies in vitro and in mouse suggest that the limited activity of oral ciprofloxacin alone is related to the inability of ciprofloxacin to achieve bactericidal concentrations at the site of infection (Inderlied et al, 1989); the minimum inhibitory concentration (MIC) of 5 µg/ml versus the clinical serum Cmax of 4 µg/ml explains the limited efficacy in experimental models and in humans (Inderlied et al, 1989). *M. abscessus* is often resistant to clarithromycin. IV aminoglycosides or imipenem need to be applied, which often are the only available therapeutic alternatives, and these carry the potential for serious side-effects, as well as the trauma and cost associated with IV administration. Clofazimine, linezolid, and cefoxitin are also sometimes prescribed, but toxicity and/or the need for IV administration limit the use of these compounds. Thus, the available therapies have significant deficiencies and improved approaches are needed.

Recent studies also showed that both *M. avium* and *M. abscessus* infections are associated with significant biofilm formation (Bermudez et al, 2008; Carter et al, 2003): deletion of biofilm-associated genes in *M. avium* had impact on the ability of the bacterium to form biofilm and to cause pulmonary infection in an experimental animal model (Yamazaki et al, 2006).

Ciprofloxacin is a broad-spectrum fluoroquinolone antibiotic that is active against several other types of gram-negative and gram-positive bacteria and is indicated for oral and IV treatment of lower respiratory tract infections. It acts by inhibition of topoisomerase II (DNA gyrase) and topoisomerase IV, which are enzymes required for bacterial replication, transcription, repair, and recombination. This mechanism of action is different from that for penicillins, cephalosporins, aminoglycosides, macrolides, and tetracyclines, and therefore bacteria resistant to these classes of drugs may be susceptible to ciprofloxacin. There is no known cross-resistance between quinolones—the class of antimicrobials that ciprofloxacin belongs to—and other classes of antimicrobials.

Despite its attractive antimicrobial properties, ciprofloxacin does produce bothersome side effects, such as GI intolerance (vomiting, diarrhea, abdominal discomfort), as well as dizziness, insomnia, irritability and increased levels of anxiety. There is a clear need for improved treatment regimes that can be used chronically, without resulting in these debilitating side effects.

Delivering ciprofloxacin as an inhaled aerosol has the potential to address some of these concerns by compartmentalizing the delivery and action of the drug in the respiratory tract, which is the primary site of infection. Currently there is no aerosolized form of ciprofloxacin with regulatory approval for human use, capable of targeting antibiotic delivery direct to the area of primary infection. In part this is because the poor solubility and bitterness of the drug have inhibited development of a formulation suitable for inhalation; many patients with airway disease may cough or bronchoconstrict when inhaling antibiotics which are not encapsulated in liposomes (Barker et al, 2000). Furthermore, the tissue distribution of ciprofloxacin is so rapid that the drug residence time in the lung is too short to provide additional therapeutic benefit over drug administered by oral or IV routes (Bergogne-Berezin E, 1993).

The therapeutic properties of many drugs are improved by incorporation into liposomes. Phospholipid vehicles as drug delivery systems were rediscovered as "liposomes" in 1965 (Bangham et al., 1965) The general term "liposome" covers a variety of structures, but all consist of one or more lipid bilayers enclosing an aqueous space in which hydrophilic drugs, such as ciprofloxacin, can be encapsulated. Liposome encapsulation improves biopharmaceutical characteristics through a number of mechanisms including altered drug pharmacokinetics and biodistribution, sustained drug release from the carrier, enhanced delivery to disease sites, and protection of the active drug species from degradation. Liposome formulations of the anticancer agents doxorubicin (Myocet®/Evacet®, Doxyl®/Caelyx®), daunorubicin (DaunoXome®) the anti-fungal agent amphotericin B (Abelcet®, AmBisome®, Amphotec®) and a benzoporphyrin (Visudyne®) are examples of successful products introduced into the US, European and Japanese markets over the last two decades. Recently a liposomal formulation of vincristine (Marqibo®) was approved for an oncology indication. The proven safety and efficacy of lipid-based carriers make them attractive candidates for the formulation of pharmaceuticals.

Therefore, in comparison to the current ciprofloxacin formulations, a liposomal ciprofloxacin aerosol formulation should offer several benefits: 1) higher drug concentrations, 2) increased drug residence time via sustained release at the site of infection, 3) decreased side effects, 4) increased palatability, 5) better penetration into the bacterial biofilms, and 6) better penetration into the cells infected by bacteria.

In one example of the current invention, the liposomes encapsulating ciprofloxacin are unilamellar vesicles (average particle size 75-120 nm). Ciprofloxacin is released slowly from these liposomes with a half-life of about 10 hours in the lung (Bruinenberg et al, 2010 b), which allows for once-a-day dosing. Further, studies with a variety of liposome compositions in in vitro and murine infection models showed that liposomal ciprofloxacin is effective against several intracellular pathogens, including *M. avium*. Inhaled liposomal ciprofloxacin is also effective in treating *Pseudomonas aeruginosa* (PA) lung infections in patients (Baton et al, 2009 a, b, 2010, 2011; Bruinenberg et al, 2008, 2009, 2010 a, b, c, d, 2011; Serisier et al, 2013).

Compared to approved doses of oral and IV ciprofloxacin, liposomal ciprofloxacin formulations delivered by inhalation into the airways achieve much greater concentrations in the respiratory tract mucosa and within macrophages with resulting improvement of clinical efficacy: 2 hours post-inhalation of a therapeutic dose of our liposomal ciprofloxacin in patients, the concentration of ciprofloxacin in the sputum exceeded 200 µg/ml, and even 20 hours later (2 hours prior to the next dose), the concentration was >20 µg/ml, well above the minimum inhibitory concentration above for resistant mycobacteria (breakpoint of ~4 µg/ml (Bruinenberg 2010b). Since the liposomes containing ciprofloxacin are avidly ingested by macrophages, the ciprofloxacin is brought into close proximity to the intracellular pathogens, thus further increasing anti-mycobacterial concentration and thus should lead to improved efficacy of the inhaled liposomal formulation compared to other forms of ciprofloxacin. We therefore believe that even highly resistant NTM may be suppressed with our inhaled liposomal ciprofloxacin. This is significant because *M. avium* and *M. abscessus* resistance to antibiotics is common due to long-term use of systemic antibiotics in these patients. Our clinical experience with *P. aeruginosa* (PA) also shows that there is no apparent emergence of resistance following inhaled liposomal ciprofloxacin therapy: in fact, even those patients who also had resistant strains initially, responded well to therapy (Serisier et al., 2013). This is likely due to the presence of sustained overwhelming concentrations of ciprofloxacin. Furthermore, the experience with other anti-pseudomonal drugs tobramycin and colistimethate in patients with cystic fibrosis is that even patients with resistant strains of PA respond clinically well to the inhaled form of the drugs (Fiel, 2008).

Several in vitro studies have demonstrated that liposomal ciprofloxacin is efficacious against intracellular pathogens: 1) In human peripheral blood monocytes/macrophages, liposomal ciprofloxacin tested over concentrations from 0.1 to 5 µg/ml caused concentration-related reductions in intracellular *M. avium-M. intracellulare* complex (MAC) colony forming units (CFU) compared to free drug at the same concentrations (Majumdar et al, 1992); 2) In a murine macrophage-like cell line J774, liposomal ciprofloxacin decreased the levels of cell associated *M. avium* up to 43-fold and these reductions were greater than for free ciprofloxacin (Oh et al, 1995).

Once *M. avium* or *M. abscessus* infect monocytes/macrophages, the infection can then spread to the lungs, liver, spleen, lymph nodes, bone marrow, and blood. There are no published studies on the efficacy of liposomal ciprofloxacin against *M. avium* or *M. abscessus* in animal models.

A few in vivo studies have demonstrated that liposomal ciprofloxacin is efficacious against the intracellular pathogen, *F. tularensis*: Efficacy of liposomal ciprofloxacin delivered to the lungs by inhalation or intranasal instillation against inhalational tularemia (*F. tularensis* live vaccine strain (LVS) and Schu S4) in mice, was demonstrated with as little as a single dose of liposomal ciprofloxacin providing 100% protection post-exposure, and even effective post-exposure treatment for animals that already had significant systemic infection (Blanchard et al, 2006; Di Ninno et al, 1993; Conley et al, 1997; Hamblin et al, 2011; Hamblin et al, 2014; Wong et al, 2003). These studies also found that inhaled liposomal ciprofloxacin was superior to both inhaled and oral unencapsulated ciprofloxacin.

In contrast, a) free ciprofloxacin was inferior to liposomal ciprofloxacin in macrophage models of mycobacterial infections (Majumdar et al, 1992; Oh et al, 1995); b) free ciprofloxacin alone delivered to the lungs had inferior efficacy to free ciprofloxacin when tested in murine models of *F. tularensis* infection (Conley et al, 1997; Wong et al, 2003), as it is rapidly absorbed into the blood stream. A formulation made up of both free and liposomal ciprofloxacin combines the potential advantages of an initial transient high concentration of free ciprofloxacin to increase Cmax in the lungs, followed by the slow release of ciprofloxacin from the liposomal component, as demonstrated in non-CF bronchiectasis patients by Aradigm (Cipolla et al, 2011; Serisier et al, 2013). The free ciprofloxacin component also has a desirable immunomodulatory effect (U.S. Pat. Nos. 8,071,127, 8,119,156, 8,268,347 and 8,414,915).

Further, liposomal ciprofloxacin injected parenterally activates macrophages, resulting in increased phagocytosis, nitric oxide production, and intracellular microbial killing even at sub-inhibitory concentrations, perhaps via immunostimulatory effects (Wong et al, 2000). The ciprofloxacin-loaded macrophages may migrate from the lungs into the lymphatics to treat infections in the liver, spleen, and bone marrow—as suggested by the systemic effects of pulmonary-delivered CFI in tularemia (Di Ninno et al, 1993; Conley et al, 1997; Hamblin et al, 2011; Hamblin et al, 2014; Wong et al, 2003). Liposome-encapsulated antibiotics are also known to better penetrate bacterial films formed by *P. aeruginosa* in the lungs (Meers et al, 2008). However, it has not been demonstrated before that antibiotic-loaded liposomes in general, or liposomally encapsulated ciprofloxacin, would be able to penetrate biofilms formed by mycobacteria, and specifically by NTM in the lung. The anti-mycobacterial and immunomodulatory effects of the new formulations delivered to the lungs, may therefore provide a better alternative to the existing treatments for patients infected with *M. avium* or *M. abscessus*, or provide an adjunct for incremental improvements if the antibiotic preparation is effective against these organisms that are planktonic, as well as in the biofilms and within macrophages. It is further required that the antibiotic treatment is well tolerated and safe when given by inhalation. Since the current antibiotic treatment options often cause serious systemic side-effects, it is desirable for the new treatment to have less toxic antibiotics and to minimize their concentration in the circulation to avoid systemic side effects.

A study of liposomal ciprofloxacin demonstrated high uptake by alveolar macrophages in animals, which is presumably the reason for the highly effective post-exposure prophylaxis and treatment of inhalational tularemia in mice. Although the plasma levels of ciprofloxacin were low following respiratory tract administration of our liposomal ciprofloxacin, a reduction of the tularemia infection from the liver, spleen, tracheobronchial lymph nodes, as well as the lungs, was observed suggesting that the alveolar macrophages loaded with liposomal ciprofloxacin migrate from the lungs via lymph into the liver, spleen and lymph nodes (*F. tularensis* CFU levels in bone marrow and blood were not measured) (Conley et al, 1997).

SUMMARY OF THE INVENTION

The current clinical paradigm is to treat patients with *M. avium* or *M. abscessus* lung infections with combination therapy given orally or by IV. But the current treatment methods have many issues, as discussed above, and do not have good efficacy. The formulation of the invention is an inhaled liposomal ciprofloxacin formulation with improved efficacy for NTM patients and allows for once daily inhalation that may be combined with other treatments. Inhaled liposomal ciprofloxacin of the invention provides for systemic therapy against *M. avium* disseminated infection, working in synergy with other antibiotics and achieving high concentrations in the lung. The transport of the macrophage-ingested liposomal ciprofloxacin via the lymphatics to the spleen and liver may occur, as observed in the murine model of *F. tularensis*.

The method of treating a non-tuberculous mycobacteria infection comprises:

aerosolizing a dose of a formulation to create aerosolized particles having an aerodynamic diameter in a range of 1 micron to 12 microns, or 2 microns to 10 microns, or 4 microns to 8 microns, and inhaling the aerosolized particles into the patient's lungs about once a day for about seven to 56 days or until the infection is eradicated.

The formulation is comprised of an anti-infective drug which may be ciprofloxacin. The formulation may include a liquid carrier which may be liquid drug or an inert liquid such as water or ethanol. The carrier may have drug dissolved or dispersed therein.

The carrier will have liposomes dispersed therein and the liposomes encapsulate nanocrytals of an anti-infective pharmaceutically active drug which may be ciprofloxacin. The liposomes are comprised of a lipid bilayer which initially encapsulates a solution of carrier and drug, followed by freezing to −20° C. to −80° C., followed by thawing whereby drug nanocrystals remain inside the liposome bilayer.

The liposomes may be comprised of a cryopreservative and a surfactant. The cryopreservative may be a polyol, e.g. sucrose or trehalose. The surfactant is a nonionic detergent which may be polysorbate 20 and/or BRIJ 20.

The invention further includes use of a formulation to treat non-tuberculous mycobacteria wherein the formulation is produced by a particular method whereby the drug such as ciprofloxacin is dissolved in an aqueous solution at a concentration in a range of 25 mg/mL or more, 50 mg/mL or more, 100 mg/mL or more, 200 mg/mL or more and encapsulated into a lipid bilayer of liposomes. The liposomes are then included within a solution which may include an anti-infective which may be the same or different from the anti-infective compound encapsulated within the liposomes and as such may be ciprofloxacin. The formulation is frozen such as being frozen at very low temperatures in the range of −20° C. to −80° C. The frozen formulation may be maintained frozen over long periods of time for storage such as one week or more, one month or more, one year or more or may be immediately rethawed for use. Upon rethawing drug inside of the liposomes forms nanocrystals. Upon administration the drug dissolved in the solvent carrier surrounding the liposomes provides for immediate release of drug followed by a drug being released when the liposomes dissolve in the lung followed by an additional release of drug when the nanocrystals dissolve. The formulation provides for controlled release of an anti-infective drug such as ciprofloxacin over a long period of time in the lungs thereby making it possible to effectively eradicate infections which occur as a biofilm.

The combination of the encapsulation of ciprofloxacin in liposomes with direct delivery of the formulation to the lungs makes these treatments fundamentally different from oral and parenteral products of ciprofloxacin and other antibiotics in terms of biodistribution, pharmacokinetics, as well as improved safety and efficacy. The liposome-encapsulated ciprofloxacin is delivered at very high concentrations directly to the respiratory tract where it resides over a prolonged period of time, during which ciprofloxacin is slowly released from the liposomes to the site of infection in the lung, and with lower systemic exposure compared to oral or IV ciprofloxacin.

The size and composition of the liposomal ciprofloxacin formulations are designed to facilitate uptake by the macrophages in the lung. The most important feature is that the formulation should be robust to the nebulization process so that the liposomes retain their size and encapsulation characteristics. If the liposomes are not robust to aerosolization, then there could be loss of encapsulated drug, or a change in the liposome size or surface characteristics. Either of these changes, or others that have not been described, might lead to lower uptake of the liposomes by macrophages. The liposomes that lose a portion of their encapsulated drug during nebulization or aerosolization, even if they are taken up by the liposomes with the same efficiency as uncompromised liposomes, now have less encapsulated drug and thus a lower payload to treat the infectious agent inside the macrophages and in biofilms thereby reducing the efficacy of treatment.

One particular composition of liposomes, which are covered by this invention, are relatively uncompromised by the nebulization process and have been described in U.S. Pat. Nos. 8,071,127, 8,119,156, 8,268,347 and 8,414,915. Those patents describe an aerosolizable, bi-phasic aerosol of inhaled droplets or particles. The droplets or particles comprise a free drug (e.g., an anti-infective compound) in which drug is not encapsulated and which may be ciprofloxacin. The particles further comprise a liposome which encapsulates a drug such as an anti-infective compound which also may be ciprofloxacin. The free and liposome encapsulated drug are included within a pharmaceutically acceptable excipient which is formulated for aerosolized delivery. The particles may further include an additional therapeutic agent which may be free and/or in a liposome and which can be any pharmaceutically active drug which is different from the first drug.

Other liposome compositions include those which are modified by nebulization, leading to changes in vesicle size, or drug encapsulation, or both. These include liposomes containing drugs such as amikacin that have been described in U.S. Pat. Nos. 8,226,975, 8,642,075, 8,673,348, 8,673,349, and U.S. Patent applications: 2007196461, 20130028960, 20130052260, 20130064883, 20130071469, 20130087480, 20130330400, 20140072620. US Patent application 20130330400 specifically describes a liposomal formulation of amikacin that is compromised by nebulization such that only 58 to 73% of the drug remains encapsulated after exposure to nebulization. In this application, US Patent application 20130330400, the mean vesicle size was also affected by the nebulization process with a reduction from a mean of 285 nm prior to nebulization to 265 nm after nebulization (range: 249 to 289 nm). US Patent application 20140072620 also describes a liposomal amikacin formulation that degrades to 60% encapsulated and 40% free drug after nebulization.

Liposomes used in connection with the present invention retain 80% or more, and preferably 90% or more, and most preferably 95% or more of the encapsulated drug after nebulization relative to that which was encapsulated prior to nebulization. If significant amounts of the drug are lost from the liposomes during nebulization, for example, greater than 20% of the encapsulated drug, then during liposome uptake by the macrophages, assuming that was designed into the feature set of the liposomes, there will be less encapsulated drug to be released into the macrophages, thereby compromising in vivo efficacy. This is a key element in the ability of the liposomal formulation to be active against the intracellular infections. Even if one conducts in vitro or in vivo studies and is able to demonstrate efficacy in those models, in the real world situation the formulation will be nebulized first, or otherwise aerosolized, so there is no assurance about the validity of the results in the model unless the formulation was applied as an aerosol (which is not typical), or other studies have been conducted to verify that the integrity of the liposomes is maintained following aerosolization.

The alveolar macrophages are targeted by *M. avium* and *M. abscessus* (Jordao et al, 2008) and other mycobacteria species as well. The macrophages avidly ingest both the liposomal ciprofloxacin and the mycobacteria, bringing both into close proximity within the phagosomes. This increase in the bioavailability at the infected target, the alveolar macrophage cells in the lung, provides improved efficacy versus systemically delivered ciprofloxacin or other anti-mycobacterial agents. The sustained-release of ciprofloxacin from the liposomes further increases the ratio of the area under the curve to MIC (AUC/MIC) in the lungs and macrophages, in particular, and may enable once-a-day dosing. The administration of these formulations provides a lower incidence of relapse and reduced adverse systemic effects.

An aspect of the invention is an aerosol of inhaled droplets or particles. The droplets or particles comprise a free drug (e.g., an anti-infective compound) in which drug is not encapsulated and which may be ciprofloxacin. The particles further comprise a liposome which encapsulates a drug such as an anti-infective compound which also may be ciprofloxacin. The free and liposome encapsulated drug are included within a pharmaceutically acceptable excipient which is formulated for aerosolized delivery. The particles may further include an additional therapeutic agent which may be free and/or in a liposome and which can be any pharmaceutically active drug which is different from the first drug.

Another aspect of the invention is a formulation comprising liposomes which are delivered via an aerosol to the lungs of a human patient with an NTM infection, or to prevent an NTM infection, the liposomes comprising free and encapsulated ciprofloxacin. The liposomes may be unilamellar or multilamellar. The aerosolization can be achieved by nebulization, including jet nebulization or mesh nebulization. The encapsulated ciprofloxacin is in liposomes which are robust to the nebulization process and maintain their encapsulation state to greater than 90% following nebulization, and preferably to greater than 95% following nebulization.

A third aspect of the invention is a method for treating intracellular infections in a patient, the method comprising administering a formulation comprising the anti-infective; e.g., ciprofloxacin, encapsulated in liposomes to the patient. The formulation is preferably administered by inhalation to the patient, and more preferably by nebulization. The intracellular infections may represent NTM infections including *M. abscessus, M. avium, M. avium* complex, (MAC) (*M. avium* and *M intracellulare*), *M. Bolletii, M. chelonae, M. ulcerans, M. xenopi, M. kansasii, M. fortuitum* complex (*M. fortuitum* and *M. chelonae*) or *M. marinum* infections.

A fourth aspect to the invention is the ability of the liposomal anti-infective formulation, preferably a liposomal ciprofloxacin formulation, after aerosolization and delivery to the airways and deep lung, to be taken up by macrophages and possess the ability to kill both replicating and non-replicating (sessile) mycobacteria. For successful treatment of NTM, it is essential that the treatment kills both replicative and dormant (or sessile) mycobacteria because both forms are found in mycobacterial infections.

The fifth aspect of the invention is that for the treatment to be maximally effective, the antibiotic formulation also needs to be able to penetrate the biofilm formed by the mycobacteria.

The sixth aspect of the invention is that the antibiotic in a suitable vehicle is not only able to penetrate the biofilm but also to have efficacy against both sessile (dormant) and replicating mycobacteria.

Another aspect of the invention is that the antibiotic does not enhance the formation of mycobacterial biofilms in the lung. In particular, *M. avium* forms biofilm, a property in mice that is associated with lung infection via aerosol. Incubation of *M. avium* with two antibiotics found in the environment, streptomycin and tetracycline, results in an increase, not decrease, in the biofilm formation. Other antibiotics, including ampicillin, moxifloxacin, rifampicin and TMP/SMX had no effect on biofilm; i.e., they were not able to kill the *M. avium*. Moxifloxacin is a fluoroquinolone, like ciprofloxacin. Accordingly, it is surprising that specific liposomal ciprofloxacin formulations of the invention are effective at killing mycobacteria in biofilm. Note that even if an antibiotic is able to kill all of the planktonic phenotype of mycobacteria, both planktonic and sessile bacteria are able to establish infection equally, ensuring that the remaining sessile bacteria will reinfect the host. Many patients with chronic lung conditions are treated for infections caused by many pathogens with antibiotics, such as aminoglycosides or tetracyclines. Therefore, in the situation that *M. avium* is colonizing an individual receiving an antibiotic, either for prophylaxis or therapy, it may result in the production of increased amounts of biofilm and further establishment of the infection.

According to another aspect of the present invention, a formulation comprising both a free and encapsulated anti-infective provides an initially high therapeutic level of the anti-infective in the lungs, while maintaining a sustained release of anti-infective over time, to overcome the barrier to eradicate the difficult to treat biofilm bacteria. The intent of the immediate-release anti-infective; e.g., ciprofloxacin, is thus to rapidly increase the antibiotic concentration in the lung to therapeutic levels around the difficult to eradicate biofilm bacteria to address the challenges of lower diffusion rate of antibiotic to and within the biofilm. The sustained-release anti-infective; e.g., ciprofloxacin, serves to maintain a therapeutic level of antibiotic in the lung thereby providing continued therapy over a longer time frame, increasing efficacy, reducing the frequency of administration, and reducing the potential for resistant colonies to form. The sustained release of the anti-infective from liposomes of the invention ensures that the anti-infective agent never falls below the sub-inhibitory concentration and so reduces the likelihood of forming resistance to the anti-infective.

Although ciprofloxacin is a particularly useful anti-infective in this invention, there is no desire to limit this invention to ciprofloxacin. Other antibiotics or anti-infectives can be used such as those selected from the group consisting of: an aminoglycoside, a tetracycline, a sulfonamide, p-aminobenzoic acid, a diaminopyrimidine, a quinolone, a beta-lactam, a beta-lactam and a beta-lactamase inhibitor, chloramphenicol, a macrolide, penicillins, cephalosporins, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, terbinafine, or any combination thereof.

Antibiotics that are effective against both dormant (sessile) and replicating bacteria are preferred.

An aspect of the invention is a formulation used for, or a method of treating a non-tuberculous mycobacteria infection, comprising:

aerosolizing a dose of a formulation to produce aerosolized particles having an aerodynamic diameter in a range of from 1 micron to 12 microns;

inhaling the aerosolizing particles into lungs of a patient, wherein the aerosolized formulation is comprised of a liquid carrier comprising free ciprofloxacin at a concentration of 20 mg/mL to 80 mg/mL of ciprofloxacin in solution, liposome unencapsulated ciprofloxacin in solution and ciprofloxacin as nanocrystals encapsulated inside the liposomes;

wherein the aerosolized particles have an aerodynamic diameter of two microns to eight microns, the liposomes have a diameter of 20 nanometers to 1 micron and the nanocrystals have dimensions of 10 nanometers or less;

wherein the ciprofloxacin is present in the solution in a concentration of 30 mg/mL to 70 mg/mL; or wherein the ciprofloxacin is present in the solution at a concentration of 40 mg/mL to 60 mg/mL;

wherein the liposomes are unilamellar and maintain structural integrity at a level of 90% or more after aerosolizing; and repeating the aerosolizing and inhaling once each day over a period of at least seven days; or wherein the repeating is carried out each day, once a day over a period of seven days to fifty six days, and wherein the infection is in a biofilm.

Another aspect of the invention is a use or method as described above further comprising:

assaying the patient for infection;

continuing the repeating aerosol administration when the patient tests positive and discontinuing when the patient tests negative;

wherein the liposomes are comprised of a cryopreservative and a surfactant;

wherein 95% or more of the liposomes maintain structural integrity and continue to encapsulate nanocrystals of ciprofloxacin after aerosolizing the formulation; or wherein 98% or more of the liposomes maintain structural integrity and continue to encapsulate nanocrystals of ciprofloxacin after aerosolizing the formulation.

Yet another aspect of the invention is a use of a formulation in treatment of non-tuberculous mycobacteria infection, wherein the formulation comprises:

liposomes wherein the liposomes comprise:

a lipid bilayer;

a cryopreservative;

and nanocrystals of a pharmaceutically active anti-infective drug surrounded by the lipid bilayer wherein the nanocrystals have dimensions of 100 nm or less;

wherein the cryopreservative is a polyol;

wherein the polyol is sucrose or trehalose;

wherein the liposomes further comprise a surfactant.

The use of the invention as described above further comprising:

a pharmaceutically acceptable carrier; or a pharmaceutically active anti-infective drug dissolved in the carrier; or a liquid anti-infective drug in which the liposomes are dispersed.

The use as described above further includes a use wherein the anti-infective drug is selected from the group comprising a quinolone, a sulfonamide, an aminoglycoside, a tetracycline, para-aminobenzoic acid, a diaminopyrimidine, a beta-lactam, a beta-lactam and a beta-lactamase inhibitor, chloramphenicol, a macrolide, lincomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, polyene antifungal, flucytosine, imidazole, triazole, griseofulvin, terconazole, butoconazole ciclopirax, ciclopirox olamine, haloprogin, tolnaftate, naftifine, terbinafine and combinations thereof, and wherein the lipid bilayer is comprised of a lipid selected from the group consisting of fatty acids; lysolipids; sphingolipids; sphingomyelin; glycolipids; glucolipids; glycosphingolipids; palmitic acid; stearic acid; arachidonic acid; oleic acid; lipids bearing sulfonated mono-, di-, oligo- or polysaccharides; lipids with ether and ester-linked fatty acids, polymerized lipids, diacetyl phosphate, stearylamine, cardiolipin, phospholipids, synthetic phospholipids with asymmetric acyl chains; and lipids bearing a covalently bound polymer; and wherein the liposome comprises a phospholipid selected from the group consisting of phosphatidylcholines, lysophosphatidylcholines, phosphatidylethanolamines, phosphatidylinositols, phosphatidylglycerols, phosphatidic acid, phosphatidylserines, and mixtures thereof; wherein said phospholipid is provided in admixtures with a modifying agent selected from the group consisting of cholesterols, stearyl amines, stearic acid, tocopherols, and mixtures thereof, and wherein the liposomes are unilamellar or multilamellar; and wherein the liposomes are comprised of HSPC and cholesterol; and wherein the lipid bilayer is comprised of HSPC and cholesterol;

the cryopreservation is selected from the group consisting of sucrose and trehalose;

the surfactant is selected from the group consisting of polysorbate 20 and BRIJ 20; and the drug is ciprofloxacin.

The invention further include any use or formulation as described here wherein liposomes are comprised of a polyol and a phosphatidylcholine-enriched phospholipids present at a ratio between 1:10 to 10:1 (w/w); and/or wherein liposomes are comprised of a polyol and a phosphatidylcholine-enriched phospholipids present at a ratio between 1:1 to 5:1 (w/w); and/or wherein the surfactant is present in an amount of between 0.01% to 1%; and/or wherein the surfactant is present in an amount between 0.05% to 0.4%; and/or wherein the infection is an infection on a biofilm in the lung of the patient and the liposomes release drug over a period of time and at a rate effective in treating a biofilm infection.

The invention also includes any use for or method of treating an antibiotic resistant infection in a patient, comprising:

aerosolizing a formulation comprising free ciprofloxacin and ciprofloxacin encapsulated in liposomes; and inhaling the aerosol into the patient's lungs whereby 90% or more of the liposomes maintain structural integrity after being aerosolized, wherein the antibiotic resistant infection comprises microorganisms in a biofilm or microorganisms engulfed in macrophage;

wherein the infection is an infection of microorganisms in a biofilm; and/or wherein the infection is an infection of microorganisms engulfed in macrophage in a planktonic state; and/or wherein the infection is an infection of microorganisms selected from the group consisting of mycobacteria, *P. aeruginosa* and *F. tularensis*; and/or the liposomes comprise a cryopreservative and a surfactant and have an average particle size of about 75 nm to about 120 nm and are unilamellar; and/or the liposomes are comprised of cholesterol and hydrogenated soy phosphatidyl-choline (HSPC)—a semi-synthetic fully hydrogenated derivative of nature soy lecithin at a ratio of about 30 to 70 (plus or minus 10%); and/or the formulation further comprising an excipient suitable for pulmonary delivery comprised of sodium acetate and an isotonic buffer; and/or 90% or more of the liposomes maintain integrity when aerosolized and after contacting lung tissue provide a ciprofloxacin release rate of 0.5% to 10% per hour; and/or 95% or more of the liposomes maintain integrity when aerosolized and after contacting lung tissue provide a ciprofloxacin release rate of 1% to 8% per hour; and/or the liposomes comprise cholesterol and hydrogenated soy phosphatidyl-choline (HSPC) at a ratio of 29.4 to 70.6, and are unilamellar and wherein 98% or more of the liposomes maintain integrity when aerosolized, and provide a ciprofloxacin release rate of 2% to 6% per hour.

The invention includes a formulation use or method described here wherein:

the liposomes are further comprised of 0.1 to 0.3% polysorbate 20, and 200 to 400 mg/mL sucrose; and/or the aerosolizing and inhaling are repeated once each day over a period of seven days or more; and/or the aerosolizing and inhaling are repeated once each day over a period of seven days to fifty-six days; and/or the formulation comprises 50 mg to 500 mg of ciprofloxacin; and/or the formulation comprises 75 mg to 300 mg of ciprofloxacin; and/or the formulation is nebulized and comprises 150 mg of ciprofloxacin.

These and other objects, advantages, and features of the invention will become apparent to those persons skilled in the al upon reading the details of the formulations and methodology as more fully described below.

BRIEF DESCRIPTION OF THE DRAWINGS

Aspects and embodiments of the invention are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following FIGURES:

FIG. 1 is a manufacturing flow chart of liposomal ciprofloxacin for inhalation (HSPC/Chol—10 L Batch)

DETAILED DESCRIPTION OF THE INVENTION

Before the present method of formulating ciprofloxacin-encapsulated liposomes and delivery of such for prevention and/or treatment of NTM infections and other medical conditions, and devices and formulations used in connection with such are described, it is to be understood that this invention is not limited to the particular methodology, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, anti-infective refers to agents that act against infections, such as bacterial, viral, fungal, mycobacterial, or protozoal infections.

Anti-infectives covered by the invention include but are not limited to quinolones (such as nalidixic acid, cinoxacin, ciprofloxacin and norfloxacin and the like), sulfonamides (e.g., sulfanilamide, sulfadiazine, sulfamethaoxazole, sulfisoxazole, sulfacetamide, and the like), aminoglycosides (e.g., streptomycin, gentamicin, tobramycin, amikacin, netilmicin, kanamycin, and the like), tetracyclines (such as chlortetracycline, oxytetracycline, methacycline, doxycycline, minocycline and the like), para-aminobenzoic acid, diaminopyrimidines (such as trimethoprim, often used in conjunction with sulfamethoxazole, pyrazinamide, and the like), penicillins (such as penicillin G, penicillin V, ampicillin, amoxicillin, bacampicillin, carbenicillin, carbenicillin indanyl, ticarcillin, azlocillin, mezlocillin, piperacillin, and the like), penicillinase resistant penicillin (such as methicillin, oxacillin, cloxacillin, dicloxacillin, nafcillin and the like), first generation cephalosporins (such as cefadroxil, cephalexin, cephradine, cephalothin, cephapirin, cefazolin, and the like), second generation cephalosporins (such as cefaclor, cefamandole, cefonicid, cefoxitin, cefotetan, cefuroxime, cefuroxime axetil, cefinetazole, cefprozil, loracarbef, ceforanide, and the like), third generation cephalosporins (such as cefepime, cefoperazone, cefotaxime, ceflizoxime, ceftriaxone, ceftazidime, cefixime, cefpodoxime, ceftibuten, and the like), other beta-lactams (such as imipenem, meropenem, aztreonam, clavulanic acid, sulbactam, tazobactam, and the like), beta-lactamase inhibitors (such as clavulanic acid), chloramphenicol, macrolides (such as erythromycin, azithromycin, clarithromycin, and the like), lincomycin, clindamycin, spectinomycin, polymyxin B, polymixins (such as polymyxin A, B, C, D, $E.sub.1$ (colistin A), or $E.sub.2$, colistin B or C, and the like) colistin, vancomycin, bacitracin, isoniazid, rifampin, ethambutol, ethionamide, aminosalicylic acid, cycloserine, capreomycin, sulfones (such as dapsone, sulfoxone sodium, and the like), clofazimine, thalidomide, or any other antibacterial agent that can be lipid encapsulated. Anti-infectives can include antifungal agents, including polyene antifungals (such as amphotericin B, nystatin, natamycin, and the like), flucytosine, imidazoles (such as miconazole, clotrimazole, econazole, ketoconazole, and the like), triazoles (such as itraconazole, fluconazole, and the like), griseofulvin, terconazole, butoconazole ciclopirax, ciclopirox olamine, haloprogin, tolnaftate, naftitine, terbinafine, or any other antifungal that can be lipid encapsulated or complexed and pharmaceutically acceptable salts thereof and combinations thereof. Discussion and the examples are directed primarily toward ciprofloxacin but the scope of the application is not intended to be limited to this anti-infective. Combinations of drugs can be used.

A biofilm is any group of microorganisms in which cells stick to each other on a surface. These adherent cells are frequently embedded within a self-produced matrix of extracellular polymeric substance (EPS). Biofilm extracellular polymeric substance, which is also referred to as slime (although not everything described as slime is a biofilm), is a polymeric conglomeration generally composed of extracellular DNA, proteins, and polysaccharides. Biofilms may form on living or non-living surfaces and can be prevalent in natural, industrial and hospital settings. The microbial cells growing in a biofilm are physiologically distinct from planktonic cells of the same organism, which, by contrast, are single-cells that may float or swim in a liquid medium.

Biofilms have been found to be involved in a wide variety of microbial infections in the body, by one estimate 80% of all infections. Infectious processes in which biofilms have been implicated include common problems such as urinary tract infections, catheter infections, middle-ear infections, formation of dental plaque, gingivitis, coating contact lenses, and less common but more lethal processes such as endocarditis, infections in cystic fibrosis, and infections of permanent indwelling devices such as joint prostheses and heart valves. More recently it has been noted that bacterial biofilms may impair cutaneous wound healing and reduce topical antibacterial efficiency in healing or treating infected skin wounds.

As used herein, "Formulation" refers to the liposome-encapsulated anti-infective, with any excipients or additional active ingredients, either as a dry powder or suspended or dissolved in a liquid.

The terms "subject," "individual," "patient," and "host" are used interchangeably herein and refer to any vertebrate, particularly any mammal and most particularly including human subjects, farm animals, and mammalian pets. The subject may be, but is not necessarily under the care of a health care professional such as a doctor.

A "stable" formulation is one in which the protein or enzyme therein essentially retains its physical and chemical stability and integrity upon storage and exposure to relatively high temperatures. Various analytical techniques for measuring peptide stability are available in the art and are reviewed in Peptide and Protein Drug Delivery, 247-301, Vincent Lee Ed., Marcel Dekker, Inc., New York, N.Y., Pubs. (1991), and Jones, A. (1993) *Adv. Drug Delivery Rev.* 10:29-90. Stability can be measured at a selected temperature for a selected time period.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the claimed methods and compositions.

Invention in General

Ciprofloxacin is a well-established and extensively utilized broad-spectrum fluoroquinolone antibiotic that is indicated for the treatment of lower respiratory tract infections, due to, for example, *P. aeruginosa*, which is common in patients with cystic fibrosis. The primary advantage of inhaled antimicrobials is that they target antibiotic delivery to the area of primary infection and bypass GI-related side effects, however, the poor solubility and bitterness of the drug have limited development of a formulation suitable for inhalation. Furthermore, the rapid tissue distribution of ciprofloxacin means a short drug residence time in the lung thus limiting therapeutic benefit over oral or IV drug administration. The liposome-encapsulated formulations of ciprofloxacin described here decrease the limitations and improves management of pulmonary infections due to NTM through improved biopharmaceutical characteristics and mechanisms such as retention of vesicle size and encapsulation following nebulization, altered drug PK and biodistribution, sustained drug release from the carrier, enhanced delivery to disease sites including intracellular infections, whereby the concentration of drug is now higher within the intracellular space.

The invention is not limited to the treatment of patients with NTM infections. In fact, there are many patients and indications for which this therapy may be beneficial, including intracellular infections and particularly those infections in alveolar macrophages and/or biofilms in the airways. However, it is particularly useful against mycobacterial infections because it is effective at killing both replicating and non-replicating bacteria, which are present in biofilm. As described by McNabe et al (2012), *M. avium* forms increasing amounts of biofilm in presence of antibiotics such as streptomycin and tetracycline, which stimulate biofilm-related gene expression in the bacterium. Once formed, biofilms are made of two distinct populations of bacteria, sessile, the more resistant phenotype, and planktonic, a susceptible phenotype. This it is indeed surprising that inhaled liposomal ciprofloxacin is effective at killing both populations of bacteria, including sessile, which are more resistant. This should be contrasted to a much weaker efficacy of unencapsulated ciprofloxacin. The difference between liposomal and encapsulated ciprofloxacin activity against NTM would be likely to be even greater in vivo because the unencapsulated ciprofloxacin disappears from the airways and the lung much faster than the encapsulated ciprofloxacin.

The formulations of the invention may be administered to a patient using a disposable package and portable, hand-held, battery-powered device, such as the AERx device (U.S. Pat. No. 5,823,178, Aradigm, Hayward, Calif.). Alternatively, the formulations of the instant invention may be carried out using a mechanical (non-electronic) device. Other inhalation devices may be used to deliver the formulations including conventional jet nebulizers, ultrasonic nebulizers, soft mist inhalers, dry powder inhalers (DPIs), metered dose inhalers (MDIs), condensation aerosol generators, and other systems. The proportion of free ciprofloxacin to encapsulated ciprofloxacin was shown to remain constant after nebulization; i.e., there was no damage to the liposomes during nebulization that would result in premature release of a portion of the encapsulated antibiotic. This finding is unexpected based upon prior literature reports (Niven R W and Schreier H, 1990) but ensures that the animal or human inhaling the aerosol will get a reproducible proportion of free to encapsulated drug depositing throughout the lung.

An aerosol may be created by forcing drug through pores of a membrane which pores have a size in the range of about 0.25 to 6 microns (U.S. Pat. No. 5,823,178). When the pores have this size the particles which escape through the pores to create the aerosol will have a diameter in the range of 0.5 to 12 microns. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that an object of some embodiments is to provide aerosolized particles having a diameter in the range of about 0.5 to 12 microns.

The liposome formulation may be a low viscosity liquid formulation. The viscosity of the drug by itself or in combination with a carrier should be sufficiently low so that the formulation can be forced out of openings to form an aerosol, e.g., using 20 to 200 psi to form an aerosol preferably having a particle size in the range of about 0.5 to 12 microns.

In an embodiment, a low boiling point, highly volatile propellant is combined with the liposomes of the invention and a pharmaceutically acceptable excipient. The liposomes may be provided as a suspension or dry powder in the propellant, or, in another embodiment, the liposomes are dissolved in solution within the propellant. Both of these formulations may be readily included within a container which has a valve as its only opening. Since the propellant is highly volatile, i.e. has a low boiling point, the contents of the container will be under pressure.

In accordance with another formulation, the ciprofloxacin-containing liposomes are provided as a dry powder by itself, and in accordance with still another formulation, the ciprofloxacin-containing liposomes are provided in a solution formulation. The dry powder may be directly inhaled by allowing inhalation only at the same measured inspiratory flow rate and inspiratory volume for each delivery. The powder may be dissolved in an aqueous solvent to create a solution which is moved through a porous membrane to create an aerosol for inhalation. Any formulation which makes it possible to produce aerosolized forms of ciprofloxacin-containing liposomes which can be inhaled and delivered to a patient via the intrapulmonary route may be used in connection with the present invention. Specific information regarding formulations which can be used in connection with aerosolized delivery devices are described within Remington's Pharmaceutical Sciences, A. R. Gennaro editor (latest edition) Mack Publishing Company.

Regarding insulin formulations, it is also useful to note the findings of Sciarra et al., (1976). When low boiling point propellants are used, the propellants are held within a pressurized canister of the device and maintained in a liquid state. When the valve is actuated, the propellant is released and forces the active ingredient from the canister along with the propellant. The propellant will "flash" upon exposure to the surrounding atmosphere, i.e., the propellant immediately evaporates. The flashing occurs so rapidly that it is essentially pure active ingredient which is actually delivered to the lungs of the patient.

Based on the above, it will be understood by those skilled in the art that a plurality of different treatments and means of administration can be used to treat a single patient Thus, patients already receiving such medications, for example, as intravenous ciprofloxacin or antibiotics, etc., may benefit from inhalation of the formulations of the present invention. Some patients may receive only ciprofloxacin-containing liposome formulations by inhalation. Such patients may be diagnosed as having NTM lung infections, or have symptoms of a medical condition, which symptoms may benefit from administration to the patient of an antibiotic such as ciprofloxacin. The formulations of the invention may also be used diagnostically.

A patient will typically receive a dose of about 0.01 to 10 mg/kg/day of ciprofloxacin 20% or 10%. This dose will typically be administered by at least one, preferably several "puffs" from the aerosol device. The total dose per day is preferably administered at least once per day, but may be divided into two or more doses per day. Some patients may benefit from a period of "loading" the patient with ciprofloxacin with a higher dose or more frequent administration over a period of days or weeks, followed by a reduced or maintenance dose. As NTM is a difficult condition to treat, patients are expected to receive such therapy over a prolonged period of time.

The invention includes a method of treating non-tuberculous mycobacteria whereby the formulation of the invention is administered by any known route of administration such as injection, inhalation, nasal administration, orally, and IV infusion Although a preferred method of administration is by inhalation in that the invention is particularly suited for the treatment of infections in the form of biofilms in the lungs. The formulations of the invention are particular suited for the eradication of infections formed as biofilms in the lung for a number of reasons. First, the liposomes of the invention are particular resistant to rupture upon aerosolization in that 90% or more, 95% or more, 98% or more of the liposomes maintain their structural integrity and thereby maintain the drug formulations held within them after being aerosolized either by a nebulizer or being moved through the pores of a porous membrane. After the formulation reaches lung tissue drug dissolved in the solvent carrier which may be an aqueous carrier at a relatively low pH such as 6.5 or less, 6.0 or less, 5.5 or less, 5.0 or less drug in that carrier provides for immediate release and contact with bacteria. Thereafter, the liposomes dissolve or become more permeable and provide for release of formulation encapsulated within the liposomes. Thereafter, the nanocrystals slowly dissolve, when present inside the liposomes. Accordingly, the formulations of the invention can be delivered on a once a day basis and provided for controlled release of the drug such as ciprofloxacin over a long period of time.

Biofilms are resistant to eradication by antibiotics due to a number of factors. First, they are usually surrounded by a dense exopolysaccharide matrix that inhibits the diffusion of some antibiotics, including aminoglycosides as a class, into the biofilm. Second, the outer layer of faster-growing bacteria cells also "protects" the cells in the interior of the biofilm from antibiotic exposure. Third, the cells in the interior of the biofilm are oxygen-deprived and so are slower-growing or dormant and thus intrinsically less sensitive to antibiotic exposure. Finally, there is evidence of the presence of "persister" cells which are invulnerable to killing and other unknown resistance mechanisms may also exist.

EXPERIMENTAL

The following examples are put forth so as to provide those of ordinary skill in the art with a complete disclosure and description of how to make and use the present invention, and are not intended to limit the scope of what the inventors regard as their invention nor is it intended to represent that the experiment below is the only experiment performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Manufacture of Encapsulated Ciprofloxacin:

Ciprofloxacin (50 mg/mL) is encapsulated into liposomes consisting of hydrogenated soy phosphatidyl-choline (HSPC) (70.6 mg/mL), a semi-synthetic fully hydrogenated derivative of natural soy lecithin (SPC), and cholesterol (29.4 mg/mL). The lipid is organized in a bilayer, with an average particle size of 75 to 120 nm. The sterile suspension is suspended in an isotonic buffer (25 mM histidine, 145 mM NaCl at pH 6.0, 300 mOsm/kg) and administered by inhalation. These liposomal ciprofloxacin preparations contained approximately 1% unencapsulated ciprofloxacin.

The manufacturing process includes the following steps.
1. Preparation of buffers.
2. Weighing of lipid components.
3. Dissolution of lipids in solvent (tBuOH:EtOH:dH2O/ 49:49:2).
4. Mixing of the solvent solution of lipids with methylamine sulphate buffer (10% v/v solvent) to form multilamellar vesicles (MLVs) with encapsulated methylamine sulphate buffer at 30 mg/mL lipid.
5. Extrusion through four stacked 80 nm pore size polycarbonate filters to generate large unilamellar vesicles (LUVs). A second extrusion pass was performed to generate liposomes with a mean diameter of—. 100 nm.
6. Ultrafiltration to concentrate the liposomes to—55 mg/mL total lipid.
7. Diafiltration against 10 volumes of buffer (145 mM NaCl, 5 mM histidine, pH 6.0) to remove ethanol and generate a transmembrane pH gradient.
8. Determination of the lipid concentration by HPLC.
9. Heating of the liposome suspension to 50° C. and slow addition of powdered ciprofloxacin (60% of the total lipid mass) with stirring. Ciprofloxacin is added incrementally (10% of mass every 4 minutes over a 40-minute period) and the product incubated at 50° C. for 20 minutes following addition of the last aliquot to allow completion of the drug loading process.
10. Diafiltration of the ciprofloxacin loaded liposomes against 3-volumes of 145 mM NaCl, 5 mM acetate, pH 4.0 to remove unencapsulated ciprofloxacin under conditions in which the free ciprofloxacin is soluble.
11. Diafiltration of the ciprofloxacin loaded liposomes against 5-volumes of 145 mM NaCl, 25 mM histidine, pH 6.0 to remove any remaining un-encapsulated ciprofloxacin, further reducing the residual solvent levels and exchanging the external buffer for the desired final product buffer.

12. Ultrafiltration of the formulation to a ciprofloxacin concentration of 50 mg/mL (in-process testing required).

13. Pre-filtration of the liposomes through 0.45/0.2 gm filter sheets to remove particulates which can clog sterilizing grade filters. The filters employed are in fact sterilizing grade filters; however they are employed at elevated pressures not compatible with their use for sterile filtration.

14. Redundant filtration through 0.2 gm sterilizing grade filters.

15. Sample vialing and packaging.

The overall manufacturing scheme is shown in FIG. 1.

Example 2

Activity of Liposomal Ciprofloxacin Against *M. avium* and *M. abscessus* in Biofilm.

Preparation of Liposomal Encapsulated Ciprofloxacin and Free Ciprofloxacin:

A solution of unencapsulated, or "free" ciprofloxacin at a concentration of 20 mg/mL in 10 mM sodium acetate, pH 3.2, was prepared. A preparation of liposomal encapsulated ciprofloxacin was prepared according to Example 1 at 50 mg/mL ciprofloxacin in 25 mM histidine, 145 mM NaCl, pH 6.0.

Description of Infection Model:

Formulations containing free ciprofloxacin and liposome encapsulated ciprofloxacin, as well as an empty liposome control and buffer control, were evaluated in a *M. avium* and *M. abscessus* biofilm model on a 96 well plate for 4 days.

Design of Dose-Ranging Study:

One concentration of free or liposomal ciprofloxacin (50 or 100 mcg/mL), empty liposomes as a control, or buffer alone as a negative control were evaluated in three models. The colonization was reported initially and then on day 4.

Results:

Table 1 shows the colonization for each arm. Treatment with liposomal ciprofloxacin was found to provide a statistically significant effect in each of these models, while ciprofloxacin alone did not have a statistically significant effect.

biotic formulations, have not demonstrated the ability to decrease the number of bacteria (i.e., kill) in biofilm models of mycobacteria infections. It is likely that it is difficult to kill sessile bacteria, e.g., those found in biofilms, due to a multitude of factors, because of physical protection provided by the mycobacterial biofilm matrix, as well as phenotypic tolerance against environmental stress, including antibiotics (Islam et al.). Thus, treatment of mycobacterial biofilm infections is extremely difficult (Islam et al.). The results shown in Table 1 are thus surprising because these liposomal ciprofloxacin formulations provided substantial and effective killing of dormant or sessile bacteria. This is an essential component for treatment of NTM infections which are typically comprised of replicating and non-replicating (sessile) bacteria. Islam et al. go on to say that multiple mycobacterial species, most notably *M. avium*, have been found to exist as multicellular communities in the environment (i.e., biofilm), as well as in clinical settings. The prevalence of these mycobacterial communities in their natural habitat can be further appreciated by evidence that the aggregates and pellicles of mycobacteria, routinely observed in detergent-free in vitro cultures, represent a genetically programmed development of organized, drug-tolerant communities—the key features of biofilms.

Example 3

Activity of Liposomal Ciprofloxacin Against *M. avium* in Macrophages.

Preparation of Liposomal Encapsulated Ciprofloxacin and Free Ciprofloxacin:

A solution of unencapsulated, or "free" ciprofloxacin at a concentration of 20 mg/mL in 10 mM sodium acetate, pH 3.2, was prepared. A preparation of liposomal encapsulated ciprofloxacin was prepared according to Example 1 at 50 mg/mL ciprofloxacin in 25 mM histidine, 145 mM NaCl, pH 6.0. Samples were diluted to the appropriate concentration in the THP-1 human macrophage model.

TABLE 1

Biofilm Colonization

| Bacterial Strain | Treatment (mcg/mL) | Time 0 | Time: 4 Days | P Value |
|---|---|---|---|---|
| *M. avium* A5 | None | $3.1 \pm 0.7 \times 10^7$ | $3.4 \pm 0.5 \times 10^7$ | — |
|  | Ciprofloxacin (100) |  | $2.8 \pm 0.7 \times 10^7$ | $p > 0.05$ |
|  | Empty Liposome |  | $3.9 \pm 0.5 \times 10^7$ | $p > 0.05$ |
|  | Liposomal Ciprofloxacin (50) |  | $2.0 \pm 0.4 \times 10^7$ | $p < 0.05$ |
|  | Liposomal Ciprofloxacin (100) |  | $1.1 \pm 0.5 \times 10^7$ | $p < 0.05$ |
| *M. avium* 104 | None | $4.3 \pm 0.8 \times 10^7$ | $4.1 \pm 0.7 \times 10^7$ | — |
|  | Ciprofloxacin (100) |  | $4.0 \pm 0.3 \times 10^7$ | $p > 0.05$ |
|  | Empty Liposome |  | $4.8 \pm 0.6 \times 10^7$ | $p > 0.05$ |
|  | Liposomal Ciprofloxacin (50) |  | $2.6 \pm 0.5 \times 10^7$ | $p < 0.05$ |
|  | Liposomal Ciprofloxacin (100) |  | $1.9 \pm 0.6 \times 10^7$ | $p < 0.05$ |
| *M. abscessus* 105 | None | $3.8 \pm 0.6 \times 10^7$ | $3.9 \pm 0.8 \times 10^7$ | — |
|  | Ciprofloxacin (100) |  | $3.0 \pm 0.5 \times 10^7$ | $p > 0.05$ |
|  | Empty Liposome |  | $3.9 \pm 0.6 \times 10^7$ | $p > 0.05$ |
|  | Liposomal Ciprofloxacin (50) |  | $3.6 \pm 0.4 \times 10^7$ | $p > 0.05$ |
|  | Liposomal Ciprofloxacin (100) |  | $1.6 \pm 0.5 \times 10^7$ | $p < 0.05$ |

Conclusion:

Only liposomal ciprofloxacin formulations demonstrated killing of mycobacteria, in the biofilm. This is unprecedented as other antibiotics, including other liposomal anti- Description of Infection Model:

Formulations containing free ciprofloxacin, liposome encapsulated ciprofloxacin, liposomes containing nanocrystals of ciprofloxacin, as well as a buffer control, were evaluated in a *M. avium* bacterial strain in THP-1 human macrophages and infection in the macrophages was measured after 4 days.

Design of Study:

One concentration of free or liposomal ciprofloxacin (20 mcg/mL), or buffer alone as a negative control, were evaluated in two models. The bacterial colonization was reported initially and then on day 4.

Results:

Table 2 shows the colonization for each arm. Treatment with liposomal ciprofloxacin was found to provide a statistically significant effect in each of these macrophage infection models, while ciprofloxacin alone did not have a statistically significant effect.

TABLE 2

Colonization of *M. avium* in macrophages

| Bacterial Strain | Treatment (mcg/mL) | Time 0 | Time: 4 days | P Value |
|---|---|---|---|---|
| *M. avium* 101 | None | $7 \pm 0.2 \times 10^4$ | $5.5 \pm 0.2 \times 10^5$ | — |
| | Ciprofloxacin (20) | | $4.9 \pm 0.4 \times 10^5$ | $p > 0.05$ |
| | Liposomal Ciprofloxacin (20) | | $8.1 \pm 0.3 \times 10^3$ | $p < 0.05$ |
| | Liposomal Ciprofloxacin in nanocrystal form | | $9.6 \pm 0.4 \times 10^3$ | $p < 0.05$ |
| *M. avium* 104 | None | $1.4 \pm 0.6 \times 10^4$ | $6.0 \pm 0.5 \times 10^4$ | — |
| | Ciprofloxacin (20) | | $1.1 \pm 0.4 \times 10^4$ | $p > 0.05$ |
| | Liposomal Ciprofloxacin (20) | | $3.9 \pm 0.5 \times 10^3$ | $p < 0.05$ |
| | Liposomal Ciprofloxacin in nanocrystal form | | $7.4 \pm 0.3 \times 10^3$ | $p < 0.05$ |

Conclusion:

Both liposomal ciprofloxacin formulations have superior activity to free ciprofloxacin against *M. avium* macrophage infection models.

Example 4

Activity of Liposomal Ciprofloxacin Against *M. abscessus* in Macrophages.

Preparation of Liposomal Encapsulated Ciprofloxacin and Free Ciprofloxacin:

A solution of unencapsulated, or "free" ciprofloxacin at a concentration of 20 mg/mL in 10 mM sodium acetate, pH 3.2, was prepared. A preparation of liposomal encapsulated ciprofloxacin was prepared according to Example 1 at 50 mg/mL ciprofloxacin in 25 mM histidine, 145 mM NaCl, pH 6.0. Samples were diluted to the appropriate concentration in the THP-1 human macrophage model.

Description of Infection Model:

Formulations containing free ciprofloxacin, liposome encapsulated ciprofloxacin, empty liposomes, as well as a buffer control, were evaluated in a *M. abscessus* bacterial strain in THP-1 human macrophages and infection in the macrophages was measured after 4 days.

Design of Dose-Ranging Study:

One concentration of free or liposomal ciprofloxacin (10 or 20 mcg/mL), empty liposomes, or buffer alone as a negative control, were evaluated in two *M. abscessus* models. The bacterial colonization was reported initially and then on day 4.

Results:

Table 3 shows the colonization for each arm. Treatment with liposomal ciprofloxacin was found to provide a statistically significant effect in each of these macrophage infection models, while ciprofloxacin alone did not have a statistically significant effect.

TABLE 3

Colonization of *M. avium* in macrophages

| Bacterial Strain | Treatment (mcg/mL) | Time 0 | Time: 4 days | P Value |
|---|---|---|---|---|
| *M. abscessus* 101 | None | $3.2 \pm 0.4 \times 10^5$ | $3.6 \pm 0.3 \times 10^6$ | — |
| | Ciprofloxacin (10) | | $3.2 \pm 0.4 \times 10^6$ | $p > 0.05$ |
| | Ciprofloxacin (20) | | $1.9 \pm 0.5 \times 10^6$ | $p = 0.07$ |
| | Empty Liposomes | | $3.9 \pm 0.5 \times 10^6$ | $p > 0.05$ |
| | Liposomal Cip (10) | | $5.1 \pm 0.4 \times 10^3$ | $p < 0.05$ |
| | Liposomal Cip (20) | | $3.0 \pm 0.3 \times 10^3$ | $p < 0.05$ |
| *M. abscessus* 102 | None | $4.1 \pm 0.6 \times 10^5$ | $3.3 \pm 0.5 \times 10^6$ | — |
| | Ciprofloxacin (10) | | $3.0 \pm 0.5 \times 10^6$ | $p > 0.05$ |
| | Ciprofloxacin (20) | | $1.2 \pm 0.3 \times 10^6$ | $p = 0.068$ |
| | Empty Liposomes | | $4.6 \pm 0.5 \times 10^6$ | $p > 0.05$ |
| | Liposomal Cip (10) | | $6.7 \pm 0.3 \times 10^3$ | $p < 0.05$ |
| | Liposomal Cip (20) | | $4.2 \pm 0.6 \times 10^3$ | $p < 0.05$ |

Conclusion:

Liposomal ciprofloxacin formulations have superior activity to free ciprofloxacin against *M. abscessus* macrophage infection models.

Example 5

Activity of Liposomal Ciprofloxacin Against *M. abscessus* in Macrophages.

Preparation of Liposomal Encapsulated Ciprofloxacin and Free Ciprofloxacin:

A solution of unencapsulated, or "free" ciprofloxacin at a concentration of 20 mg/mL in 10 mM sodium acetate, pH 3.2, was prepared. A preparation of liposomal encapsulated ciprofloxacin was prepared according to Example 1 at 50 mg/mL ciprofloxacin in 25 mM histidine, 145 mM NaCl, pH 6.0. Samples were diluted to the appropriate concentration in the THP-1 human macrophage model.

Description of Infection Model:

Formulations containing free ciprofloxacin, liposome encapsulated ciprofloxacin, empty liposomes, as well as a buffer control, were evaluated in a *M. abscessus* bacterial strain in THP-1 human macrophages and infection in the macrophages was measured after 4 days.

Design of Study:

One concentration of free or liposomal ciprofloxacin (200 mcg/mL), empty liposomes, or buffer alone as a negative control, were evaluated in two *M. abscessus* models. The bacterial colonization was reported initially and then on day 4.

Results:

Table 4 shows the colonization for each arm. Treatment with liposomal ciprofloxacin was found to provide a statistically significant effect in each of these macrophage infection models, while unencapsulated ciprofloxacin alone did not have a statistically significant effect.

TABLE 4

Colonization of *M. avium* or *M. abscessus* in macrophages

| Bacterial Strain | Treatment (mcg/mL) | Time 0 | Time: 4 days | P Value |
|---|---|---|---|---|
| *M. avium* 104 | None | $2.9 \pm 0.5 \times 10^5$ | $3.6 \pm 0.5 \times 10^6$ | — |
| | Ciprofloxacin (200) | | $5.0 \pm 0.3 \times 10^4$ | p < 0.05 |
| | Empty Liposomes | | $3.9 \pm 0.2 \times 10^6$ | p > 0.05 |
| | Liposomal Ciprofloxacin (200) | | $7.1 \pm 0.3 \times 10^2$ | p < 0.05 |
| *M. abscessus* 101 | None | $2.6 \pm 0.4 \times 10^5$ | $3.2 \pm 0.6 \times 10^6$ | — |
| | Ciprofloxacin (200) | | $4.4 \pm 0.6 \times 10^4$ | p < 0.05 |
| | Empty Liposomes | | $4.1 \pm 0.2 \times 10^5$ | p > 0.05 |
| | Liposomal Ciprofloxacin (200) | | $7.4 \pm 0.3 \times 10^2$ | p < 0.05 |

Conclusion:

High concentrations of liposomal ciprofloxacin were more effective than free ciprofloxacin in *M. abscessus* and *M. avium* macrophage infection models.

Example 6

Activity of Liposomal Ciprofloxacin Against *M. avium* in C57BL/6 Mice.

Preparation of Liposomal Encapsulated Ciprofloxacin and Free Ciprofloxacin:

A solution of unencapsulated or "free" ciprofloxacin at a concentration of 20 mg/mL ciprofloxacin HCl (equivalent to 18 mg/mL ciprofloxacin) in 10 mM sodium acetate, pH 3.2, was prepared. A preparation of liposoma encapsulated ciprofloxacin was prepared according to Example 1 at 50 mg/mL ciprofloxacin HCl (equivalent to 45 mg/mL ciprofloxacin) in 25 mM histidine, 145 mM NaCl, pH 6.0. A preparation of "Pulmaquin" (Dual-Release Ciprofloxacin for Inhalation, DRCFI) a 1:1 volume-to-volume mixture of free ciprofloxacin and liposoma encapsulated ciprofloxacin, with a ciprofloxacin HCl concentration of 35 mg/mL). Samples were diluted to the appropriate concentration for dosing the mice. Pulmaquin thus contains approximately 35 mg/mL ciprofloxacin HC, with 25 mg/mL in the encapsulated form and 10 mg/mL in the unencapsulated or free form. This is equivalent to 31.5 mg/mL ciprofloxacin of which 22.5 mg/mL is encapsulated ciprofloxacin and 9 mg/mL is unencapsulated or free ciprofloxacin. The pH of Pulmaquin is between 4 and 5, intermediate between the pH of 3.2 for the unencapsulated drug and a pH of 6.0 for the encapsulated drug.

Description of Infection Model:

Formulations containing free ciprofloxacin, liposome encapsulated ciprofloxacin, Pulmaquin, and empty liposome and saline controls were evaluated in C57BL16 mice infected via intranasal instillation with *Mycobacterium avium* subsp hominissuis (MAH) MAC104 strain, with a dose of $10^7$, and infection was allowed to develop for 1 week Design of Study:

One week after infection, treatment via intranasal instillation was initiated with either saline, empty liposome control, free ciprofloxacin, liposome encapsulated ciprofloxacin, or Pulmaquin daily at ciprofloxacin doses of 0.33, 0.66 and 1 mg/kg for 3 weeks. For the empty liposome control, the dose of empty liposome matched the lipid content of 1 mg/kg dose of liposome encapsulated ciprofloxacin. Mice were harvested and lungs and spleen plated on 7H10 agar for quantification of the bacterial load in lungs. Ten mice were used per experimental group.

Results:

Table 5 shows the bacterial loads (colony forming units, CFU) for the lung and spleen. While empty liposomes and free ciprofloxacin had no significant effect on the growth of MAH in the lungs of mice compared with saline control, administration of 1 mg/kg of liposome encapsulated ciprofloxacin or Pulmaquin was associated with a significant reduction in CFU from $(1.06\pm0.5)\times10^7$ to $(2.25\pm0.4)\times10^6$ (−79%) and $(2.47\pm0.6)\times10^6$ (−77%), respectively (p<0.05 for both vs saline or empty liposomes). Treatment with 0.33 mg/kg and 0.67 mg/kg liposome encapsulated ciprofloxacin or Pulmaquin also resulted in significant reduction of CFU in the lungs (−37 to −67%).

TABLE 5

Bacterial Loads (CFU) in Lungs and Spleen in MAH Infected Mice

| Time | Treatment | Dose (mg/kg) | Lung CFU | Spleen CFU |
|---|---|---|---|---|
| Baseline | No Treatment | | $2.0 \pm 0.4 \times 10^6$ | $5.39 \pm 0.4 \times 10^4$ |
| 3 weeks | Saline | | $1.06 \pm 0.5 \times 10^7$ | $4.72 \pm 0.3 \times 10^5$ |
| 3 weeks | Empty liposomes | 1 | $2.51 \pm 0.4 \times 10^7$ | $6.27 \pm 0.4 \times 10^5$ |
| 3 weeks | Free Ciprofloxacin | 1 | $8.65 \pm 0.4 \times 10^{6*}$ | $6.47 \pm 0.4 \times 10^5$ |
| | | 0.67 | $1.04 \pm 0.4 \times 10^7$ | $5.99 \pm 0.6 \times 10^5$ |
| | | 0.33 | $2.64 \pm 0.4 \times 10^7$ | $7.38 \pm 0.3 \times 10^5$ |
| 3 weeks | Liposomal Ciprofloxacin | 1 | $2.25 \pm 0.4 \times 10^{6**}$ | $3.13 \pm 0.4 \times 10^5$ |
| | | 0.67 | $3.72 \pm 0.5 \times 10^{6*}$ | $7.25 \pm 0.3 \times 10^5$ |
| | | 0.33 | $5.84 \pm 0.3 \times 10^{6*}$ | $8.28 \pm 0.4 \times 10^5$ |
| 3 weeks | Pulmaquin | 1 | $2.47 \pm 0.6 \times 10^{6**}$ | $6.14 \pm 0.4 \times 10^5$ |
| | | 0.67 | $3.49 \pm 0.4 \times 10^{6*}$ | $7.02 \pm 0.3 \times 10^5$ |
| | | 0.33 | $6.71 \pm 0.3 \times 10^{6*}$ | $8.30 \pm 0.5 \times 10^5$ |

*$p < 0.05$ than saline/empty
**$p < 0.05$ than free ciprofloxacin

Conclusion:

Three-week intranasal treatment of mice with lung infections from MAH with liposome encapsulated ciprofloxacin or Pulmaquin resulted in significant reduction of MAH load in the lungs.

Example 7

Activity of Liposomal Ciprofloxacin Against *M. abscessus* in Mice.

Preparation of Liposomal Encapsulated Ciprofloxacin and Free Ciprofloxacin:

A solution of unencapsulated or "free" ciprofloxacin HCl at a concentration of 20 mg/mL (equivalent to 18 mg/mL ciprofloxacin) in 10 mM sodium acetate, pH 3.2, was prepared. A preparation of liposomal encapsulated ciprofloxacin was prepared according to Example 1 at 50 mg/mL ciprofloxacin HCl (equivalent to 45 mg/mL ciprofloxacin) in 25 mM histidine, 145 mM NaCl, pH 6.0. A preparation of "Pulmaquin" (Dual-Release Ciprofloxacin for Inhalation, DRCFI) a 1:1 volume-to-volume mixture of free ciprofloxacin and liposomal encapsulated ciprofloxacin, with a ciprofloxacin HCl concentration of 35 mg/mL, equivalent to 31.5 mg/mL ciprofloxacin). Samples were diluted to the appropriate concentration for dosing the mice.

Description of Infection Model:

Formulations containing free ciprofloxacin, liposome encapsulated ciprofloxacin, Pulmaquin, and empty liposome and saline controls were evaluated in C57 BL/6J-lysbg-Ja mice infected via intranasal instillation with *Mycobacterium abscessus* strain MA26 with a dose of $(5.4 \pm 0.3) \times 10^7$, which is a clinical isolate from a patient at the National Institutes of Health, in 50 'IL of buffer (Hank Balanced Salt Solution) and infection was allowed to develop for 1 week.

Design of Study:

One week after infection, treatment via intranasal instillation was initiated with either saline, empty liposome control, free ciprofloxacin, liposome encapsulated ciprofloxacin, or Pulmaquin daily with a ciprofloxacin dose of 1 mg/kg for 3 or 6 weeks. For the empty liposome control, the dose of empty liposome matched the lipid content of 1 mg/kg dose of liposome encapsulated ciprofloxacin. Mice were harvested and lungs and spleen plated on 7H10 agar for quantification of the bacterial load in lungs. Ten mice were used per experimental group.

Results:

Table 6 shows the bacterial loads (colony forming units, CFU) for the lung and spleen. While empty liposomes and free ciprofloxacin had no significant effect on the growth of *M. abscessus* in the lungs of mice compared with the untreated control, administration of liposome encapsulated ciprofloxacin or Pulmaquin for 6 weeks was associated with significant reductions in CFU from untreated at 6 weeks $(5.4 \pm 0.6) \times 10^5$ to $(1.4 \pm 0.5) \times 10^3$ (−99.7%) and $(3.0 \pm 0.4) \times 10^3$ (−99.4%), respectively ($p < 0.05$ for both vs. untreated control). Treatment for 3 weeks with liposome encapsulated ciprofloxacin or Pulmaquin was also associated with significant reductions in CFU from untreated at 6 weeks $(5.4 \pm 0.6) \times 10^5$ to $(2.6 \pm 0.6) \times 10^4$ (−95.2%) and $(2.1 \pm 0.4) \times 10^4$ (−96.1%), respectively ($p < 0.05$ for both vs. untreated control).

TABLE 6

Bacterial Loads (CFU) in Lungs and Spleen in *M abscessus* Infected Mice

| Treatment | Weeks | Lung CFU | Spleen CFU |
|---|---|---|---|
| Baseline | 1 | $2.6 \pm 0.4 \times 10^6$ | $1.5 \pm 0.5 \times 10^4$ |
| Untreated | 6 | $5.4 \pm 0.6 \times 10^5$ | $7.3 \pm 0.4 \times 10^3$ |
| Empty Liposomes | 3 | $4.8 \pm 0.5 \times 10^5$ | $5.7 \pm 0.3 \times 10^4$ |
| Empty Liposomes | 6 | $3.6 \pm 0.3 \times 10^5$ | $3.5 \pm 0.4 \times 10^4$ |
| Free Ciprofloxacin | 3 | $5.3 \pm 0.3 \times 10^5$ | $5.5 \pm 0.4 \times 10^4$ |
| Free Ciprofloxacin | 6 | $4.0 \pm 0.4 \times 10^5$ | $2.7 \pm 0.3 \times 10^4$ |
| Liposomal Ciprofloxacin | 3 | $2.6 \pm 0.6 \times 10^{4*}$ | $2.5 \pm 0.3 \times 10^4$ |
| Liposomal Ciprofloxacin | 6 | $1.4 \pm 0.5 \times 10^{3*}$ | $9.1 \pm 0.3 \times 10^3$ |
| Pulmaquin | 3 | $2.1 \pm 0.4 \times 10^{4*}$ | $2.8 \pm 0.4 \times 10^4$ |
| Pulmaquin | 6 | $3.0 \pm 0.4 \times 10^{3*}$ | $8.2 \pm 0.5 \times 10^3$ |

*$p < 0.05$ compared controls

Conclusion:

Three- or six-week intranasal treatment of mice with lung infections from A abscessus with liposome encapsulated ciprofloxacin or Pulmaquin resulted in significant reduction of bacterial load in the lungs.

REFERENCES

Each of the following is incorporated by reference.

Adjemian J, Olivier K N, Seitz A E, Holland S M, Prevots D R, Prevalence of nontuberculosis mycobacterial lung disease in US Medicare beneficiaries. Am J Respir Crit Care Med, 185: 881-886, 2012. PMID: 22773732

Bangham A D, Standish M M, Watkins J C, Diffusion of univalent ions across the lamellae of swollen phospholipids. J Mol Biol 13 (1) (1965) 238-252.

Barker A F, Couch L, Feil S B, Gotfried M H, Ilowite J, Meyer K C, O'Donnell A, Sahn S A, Smith L J, Stewart J O, Abuan T, Tully H, Van Dalfsen J, Wells C D, Quan J. Tobramycin solution for inhalation reduces sputum *Pseudomonas aeruginosa* density in bronchiectasis. Am J Respir Crit Care Med 162: 481-5, 2000. PMID: 10934074

Bergogne-Berezin E. Pharmacokinetics of fluoroquinolones in respiratory tissues and fluids. Quinolones Bull. 10: 1-18, 1993.

Bermudez L E, Motamedi N, Kolonoski P. Chee C, Baimukanova G, Bildfell R, Wang G, Phan L T, Young L S The efficacy of clarithromycin and the bicyclolide EDP-420 against *Mycobacterium avium* in a mouse model of pulmonary infection. J Infect Dis, 197: 1506-10, 2008. PMID: 18422455

Bermudez L E, Blanchard J D, Hauck L, Gonda I. Treatment of *Mycobacterium avium* subsp hominissuis (MAH) lung infection with liposome-encapsulated ciprofloxacin resulted in significant decrease in bacterial load in the lung. Presented at American Thoracic Society (ATS) International Conference, Denver, Colo. 2015.

Bilton D, P Bruinenberg P, Otulana B. Inhaled liposomal ciprofloxacin hydrochloride significantly reduces sputum *Pseudomonas aeruginosa* density in CF and non-CF bronchiectasis. Presented at American Thoracic Society (ATS) International Conference, San Diego, Calif. Am J Respir Crit Care Med 179:A3214, 2009.

Bilton D, Bruinenberg P, Otulana B, Morishige R, Blanchard J, DeSoyza A, Serisier D. Inhaled liposomal ciprofloxacin hydrochloride significantly reduces sputum *Pseudomonas aeruginosa* density in CF and non-CF bronchiectasis. Presented at European Respiratory Society (ERS) Conference. Abstract 1362, 2009.

Bilton D, De Soyza A, Hayward C, Bruinenberg P. Effect of a 28-day course of two different doses of once a day liposomal ciprofloxacin for inhalation on sputum *Pseudomonas aeruginosa* density in non-CF bronchiectasis, Presented at American Thoracic Society (ATS) International Conference, New Orleans, La. Am J Respir Crit Care Med 181:A3191, 2010.

Bilton D, Serisier D J, DeSoyza A, Wolf R, Bruinenberg P. Multicenter, randomized, double-blind, placebo-controlled study (ORBIT 1) to evaluate the efficacy, safety, and tolerability of once daily ciprofloxacin for inhalation in the management of *Pseudomonas aeruginosa* infections in patients with non-cystic fibrosis bronchiectasis. Presented at European Respiratory Society Annual Congress, Amsterdam, The Netherlands. Abstract 1925, 2011.

Blanchard J D. Pulmonary drug delivery as a first response to bioterrorism. In: Dalby R N, Byron P R, Peart J, Suman J D, and Farr S J, eds., Respiratory Drug Delivery X, River Grove, Ill.: Davis Healthcare International, 2006, 73-82.

Blanchard J, Danelishvili L, Gonda I, Bermudez L. Liposomal ciprofloxacin preparation is active against *Mycobacterium avium* subsp hominissuis and *Mycobacterium abscessus* in macrophages and in biofilm. Presented at American Thoracic Society (ATS) International Conference, San Diego, Calif. Abstract 57372, 2014.

Bruinenberg P, Otulana B, Blanchard J. Morishige R, Cipolla D, Wilson J, Serisier D. The effect of once-a-day, inhaled liposomal ciprofloxacin hydrochloride for inhalation on bacterial density in cystic fibrosis patients with chronic *P. aeruginosa* infection. Presented at North American Cystic Fibrosis Conference, Orlando, Fla., 2008. Ped Pulmon 43 (Suppl 31):401, 2008.

Bruinenberg P, Otulana B, Blanchard J, Cipolla D, Wilson J, Serisier D.

Pharmacokinetics and antibacterial activity of inhaled liposomal ciprofloxacin hydrochloride in healthy volunteers and in cystic fibrosis (CF) patients. Presented at 32nd European Cystic Fibrosis Conference, Brest, France. J Cystic Fibrosis 8 (Suppl 2):S49, 2009.

Bruinenberg P, Blanchard J, Cipolla D, Serisier D. Safety, tolerability and phannacokinetics of novel liposomal ciprofloxacin formulations for inhalation in healthy volunteers and in non-cystic bronchiectasis patients. Presented at American Thoracic Society (ATS) International Conference, New Orleans, La. Am J Respir Crit Care Med 181:A3192, 2010.

Bruinenberg, P, Blanchard J D, Cipolla D C, Dayton F, Mudumba S, Gonda I. Inhaled liposomal ciprofloxacin: once a day management of respiratory infections. In: Dalby, R N, Byron P R, Peart J, Suman J D, Farr S J, Young P M, eds. Respiratory Drug Delivery 2010. River Grove, Ill.: Davis Healthcare International, 73-81, 2010.

Bruinenberg P, Serisier D, Blanchard J, Cipolla D, Gonda I. Effects and modulation of release rate of inhaled ciprofloxacin with liposomal formulations in healthy subjects and patients with bronchiectasis. Presented at European Respiratory Society Annual Congress, Barcelona, Spain. Abstract 1625, 2010.

Bruinenberg P, Serisier D, Cipolla D, Blanchard J. Safety, tolerability pharmacokinetics and antimicrobial activity of inhaled liposomal ciprofloxacin formulations in humans. Presented at North American Cystic Fibrosis Conference, Baltimore, Md. 45 (Suppl 33): Poster 377, 2010.

Bruinenberg P, Serisier D, Cipolla D, Blanchard J. Safety, tolerability, and pharmacokinetics of novel liposomal ciprofloxacin formulations in healthy volunteers (HV) and non-cystic fibrosis bronchiectasis (BE) patients. J Cystic Fibrosis 10 (Suppl 1): S29, 2011.

Carter G, Drummond D, Bermudez L E. Characterization of biofilm formation by *Mycobacterium avium* strains. J Med Microbiol 52: 747-52, 2003. PMID: 12909649

[Chiu J, Nussbaum J, Bozzette S, Tilles J G, Young L S, Leedom J, Heseltine P N, McCutchan J A. Treatment of disseminated *Mycobacterium avium* complex infection in AIDS with amikacin, ethambutol and ciprofloxacin. Ann Intern Med 113: 358-61, 1990. PMID: 2382918

Cipolla D C, Dayton F, Fulzele S, Gabatan E, Mudumba S, Yim D, Wu H and Zwolinski R. (2010), Inhaled Liposomal Ciprofloxacin: In Vitro Properties and Aerosol Performance. Respiratory Drug Delivery 2010. pp. 409-414. Editors, Richard N. Dalby, Peter R.

Byron, Joanne Peart, Julie D. Suman, Stephen J. Farr, Paul M. Young. Davis Healthcare Int'l Publishing, River Grove, Ill. Orlando, Fla., Apr. 25-29, 2010.

Cipolla D, Redelmeier T, Eastman S., Bruinenberg P, and Gonda I. (2011)

Liposomes, niosomes and proniosomes—a critical update of their (commercial) development as inhaled products. Respiratory Drug Delivery Europe 2011, pp 41-54. Editors, Richard N. Dalby, Peter R. Byron, Joanne Peart, Julie D. Suman, Stephen J. Fan, Paul M. Young. Davis Healthcare Int'l Publishing, River Grove, Ill. Berlin, Germany, May 3-6, 2011.

Cipolla D, Wu H, Chan J, Chan H-K, and Gonda I. (2013a) Liposomal Ciprofloxacin for Inhalation Retains Integrity Following Nebulization. Respiratory Drug Delivery Europe 2013, pp 237-242. Editors, Richard N. Dalby, Peter R. Byron, Joanne Peart, Julie D. Suman, Stephen J. Farr, Paul M. Young. Davis Healthcare Int'l Publishing, River Grove, Ill. Berlin, Germany, May 21-24, 2013.

Cipolla D, Gonda I, and Chan H-K. (2013b) Liposomal Formulations for Inhalation. Therapeutic Delivery. Vol. 4, No. 8, pp. 1047-1072. doi: 10.4155/tde.13.71.

Conley J, Yang H, Wilson T, Blasetti K, Di Ninno V, Schnell G, Wong J P. Aerosol delivery of liposome encapsulated ciprofloxacin: aerosol characterization and efficacy against *Francisella tuleransis* infection in mice. Antimicrob Agents Chemother 41: 1288-92, 1997. PMC1D: PMC163901

Costerton J W, Lewandowski Z, Caldwell D E, Korber D R, Lappin-Scott H M., Microbial biofilms. Annu Rev Microbiol. 1995; 49:711-45.

de Lalla F, Maserati R, Scarpellini P, Marone P, Nicolin R, Caccamo F, Rigoli R. Clarithromycin-ciprofloxacin-amikacin for therapy of *Mycobacterium avium-Mycobacterium intracellulare* bacteremia in patients with AIDS. Antimicrob Agents Chemother 36: 1567-9, 1992. PMCID: PMC191622

Di Ninno V L, Cherwonogrodzky J W, Wong J P. Liposome-encapsulated ciprofloxacin is effective in the protection and treatment of Balb/c mice against *Francisella tularensis*. J Infect Dis 168:793-794, 1993. PMID: 8354928

Fiel S B. Aerosolized antibiotics in cystic fibrosis: current and future trends. Expert Rev Respir Med 2: 479-487, 2008. PMID: 20477211

Fitzsimmons S C. The changing epidemiology of cystic fibrosis. J Pediatr. 1993 January; 122(1):1-9.

Fowler S J, French J, Scranton N J, Foweraker J, Condliffe A, Haworth C S, Exley A R, Bilton D. Nontuberculous mycobacteria in bronchiectasis: prevalence and patient characteristics. Eur Respir J 28: 1204-10, 2006. PMID: 16807259

Gilbert P, Das J, Foley I., Biofilm susceptibility to antimicrobials. Adv Dent. Res. 1997 April; 11(1):160-7.

Hamblin K A, Blanchard J D, Atkins H S. Efficacy of liposome-encapsulated ciprofloxacin against *Francisella tularensis* Schu S4 strain. Presented at Interscience Conference on Antimicrobial Agents and Chemotherapy (ICACC), Chicago, Ill., Poster F1-741, 2011.

Hamblin K A, Armstrong S J, Kay B, Barnes K B, Davies C, Wong J P, Blanchard J D, Harding S V, Simpson A J H, Atkins H S. Liposome-encapsulation of ciprofloxacin improves protection against highly resistant *Francisella tularensis* Schu S4 strain. Antimicrob Agents Chemother 2014 (In press) PMID: 24637682.

Inderlied C, Kolonoski P, Wu M, Young L. Amikacin, ciprofloxacin, and imipenem treatment for disseminated *Mycobacterium avium* complex infection of beige mice. Antimicrob Agents Chemother 33: 176-80, 1989. PMCID: PMC171452

Inderlied C B, Kemper C A, Bermudez L E. The *Mycobacterium avium* complex. Clin Micro Rev 6: 266-310, 1993. PMCID: PMC358286

Islam M S, Richards J P, Ojha A K. Targeting drug tolerance in mycobacteria: a perspective from mycobacterial biofilms. Expert Rev Anti Infect Ther. 10(9): 1055-1066 (2012).

Jordao L, Bleck C K, Mayorga L, Griffths G, Anes E. On the killing of mycobacteria by macrophages. Cell Microbiol 10: 529-48, 2008. PMID: 17986264

Lode H, Bonner K, Koeppe P, Schaberg T., Azithromycin-review of key chemical, pharmacokinetic and microbiological features. J Antimicrob Chemother. 1996; 37, Suppl C: 1-8

Majumdar S, Flasher D, Friend D S, Nassos P, Yajko D, Hadley W K, Diizgiines N. Efficacies of liposome-encapsulated streptomycin and ciprofloxacin against *Mycobacterium avium-M. intracellulare* complex infections in human peripheral blood monocytes/macrophages. Antimicrob Agents Chemother 36: 2808-15, 1992. PMCID: PMC245550.

McNabe M, Tennant R, Danelishvili L, Young L, Bermudez L E. *Mycobacterium avium* ssp. hominissuis biofilm is composed of distinct phenotypes and influenced by the presence of antimicrobials. Clin Microbiol Infect 17(5) 697-703 (2012). PMID: 20636426

Meers P, Neville M, Malinin V, Scotto A W, Sardaryan G, Kurumunda R, Mackinson C, James G, Fisher S, Perkins W R. Biofilm penetration, triggered release and in vivo activity of inhaled liposomal amikacin in chronic *Pseudomonas aeruginosa* lung infections, J Antimicrob Chemother, 61: 859-68, 2008. PMID: 18305202

Niven R N and Schreier H. Nebulization of Liposomes: I. Effects of Lipid Composition. Pharm Res. 1990; 7:1127-1133.

Oh Y K, Nix D E, Straubinger R M. Formulation and efficacy of liposome-encapsulated antibiotics for therapy of intracellular *Mycobacterium avium* infection. Antimicrob Agents Chemother 39: 2104-11, 1995. PMCID: PMC162889

Polonio R E Mermel L A, Paquette G E, Sperry J F., Eradication of biofilm-forming *Staphylococcus epidermidis* (RP62A) by a combination of sodium salicylate and vancomycin. Antimicrob Agents Chemother. 2001 November; 45(11):3262-6.

Prevots R D, Shaw P A, Strickland D, Jackson L A, Raebel M A, Blosky M A, Montes de Oca R, Shea Y R., Seitz A E, Holland S M, Olivier, K N. Nontuberculosis mycobacterial lung disease prevalence at four integrated health care delivery systems. Am J Respir Crit Care Med 182: 970-976, 2010 PMID: 20538958.

Serisier D J, Bilton D, De Soyza A, Thompson P J, Kolbe J, Greville H W, Cipolla D, Bninenberg P, and Gonda I. (2013) Inhaled, Dual-Release Liposomal Ciprofloxacin in Non-Cystic Fibrosis Bronchiectasis (ORBIT-2)—a Randomised, Double-Blind, Placebo-Controlled Trial. Thorax. Vol. 68, No. 9, pp. 812-817 doi: 10.1136/thoraxjnl-2013-203207.

Shafran S D, Singer J, Zarowny D P, Phillips P, Salit I, Walmsley S L, Fong I W, Gill M J, Rachlis A R, Lalonde R G, Fanning M M, Tsoukas C M. A comparison of two regimens for the treatment of *Mycobacterium avium* complex bacteremia in AIDS, rifampin, ethambutol, and clarithromycin, versus rifampin, ethambutol, clofazimine and ciprofloxacin. N Engl J Med 335: 377-83, 1996. PMID: 8676931

Smith A L, Ramsey B W, Hedges D L, Hack B, Williams-Warren J, Weber A, Gore E J, Redding G J. Safety of aerosol tobramycin administration for 3 months to patients with cystic fibrosis. Ped Pulmonol. 1989; 7(4): 265-271.

Van Heeckeren A M, Schluchter M D., Murine models of chronic *Pseudomonas aeruginosa* lung infection. Lab Anim. 2002 July; 36(3):291-312.

Van Heeckeren A M, Tscheikuna J, Walenga R W, Konstan M W, Davis P B, Erokwu B, Haxhiu M A, Ferkol T W. Effect of *Pseudomonas* infection on weight loss, lung mechanics, and cytokines in mice. Am J Respir Crit Care Med. 2000 January; 161(1):271-9.

Weber A, Smith A, Williams-Warren J, Ramsey B, Covert D S., Nebulizer delivery of tobramycin to the lower respiratory tract. Pediatr Pulmonol. 1994 May; 17(5):331-9.

Wong J P, Yang H, Blasetti K L, Schnell G, Conley J, Schofield L N. Liposome delivery of ciprofloxacin against intracellular *Francisella tularensis* infection. J Control Release 92: 265-73, 2003. PMID: 14568408

Wong J P, Schnell G, Simpson M, Saravolac E. Effects of liposome-encapsulated ciprofloxacin on phagocytosis, nitric oxide, and intracellular killing of *Staphylococcus aureus* by murine macrophages. Artific Cells Blood Substit Immobil Biotechnol 28: 415-28, 2000. PMID: 11009114

Wolter J, Seeney S, Bell S, Bowler S, Masel P, McCormack J., Effect of long term treatment with azithromycin on disease parameters in cystic fibrosis: a randomised trial. Thorax 2002; 57: 212-216.

Yamazaki Y, Danelishvili L, Wu M, Hidaka E, Katsuyama T, Stang B, Petrofsky M, Bildfell R, Bermudez L. The ability to form biofilm influences *Mycobacterium avium* invasion and translocation of bronchial epithelial cells. Cell Microbiol 8: 806-14, 2006. PMID: 16611229

Yeager H, Raleigh J W. Pulmonary disease due to *Mycobacterium intracellulare*. Am Rev Resp Dis 108: 547-52, 1973. PMID: 4745250

What is claimed is:

1. A method of treating an antibiotic resistant infection in a patient, comprising:
    administering to said patient having an antibiotic resistant infection an aerosolized pharmaceutical formulation by aerososolizing a pharmaceutical formulation to yield the aerosolized pharmaceutical formulation and providing the aerosolized pharmaceutical formulation for inhalation by the patient, the pharmaceutical formulation comprising:
        a pharmaceutically acceptable carrier, and
        liposomes in the carrier, wherein the liposomes comprise:
            a lipid bilayer,
            a cryopreservative,
            a solution of ciprofloxacin; and
            ciprofloxacin nanocrystals precipitated out of the solution of ciproflocaxin, wherein the nanocrystals are surrounded by the lipid bilayer, and wherein the nanocrystals have dimensions of 100 nm or less.

2. The method of treatment of claim 1, wherein the antibiotic resistant infection is an infection of microorganisms selected from the group consisting of *P. aeruginosa* and *F. tularensis*.

3. The method of claim 1, wherein:
    the liposomes further comprise cholesterol and hydrogenated soy phosphatidyl-choline (HSPC) at a ratio of about 30 to 70 (plus or minus 10%); and
    wherein the pharmaceutical formulation further comprising an excipient suitable for pulmonary delivery comprised of sodium acetate and an isotonic buffer; and
    wherein 90% or more of the liposomes maintain integrity when aerosolized.

4. The method of claim 1 wherein:
    95% or more of the liposomes maintain integrity when aerosolized and after contacting lung tissue provide a ciprofloxacin release rate of 1% to 8% per hour; and
    the liposomes further comprise cholesterol and hydrogenated soy phosphatidyl-choline (HSPC) at a ratio of 29.4 to 70.6, wherein the liposomes are unilamellar, and wherein 98% or more of the liposomes maintain integrity when aerosolized and provide a ciprofloxacin release rate of 2% to 6% per hour.

5. The method of claim 1 wherein:
    the pharmaceutical formulation further comprises 0.1 to 0.3% polysorbate 20, and 200 to 400 mg/mL sucrose;
    the aerosolizing and inhalation are repeated once each day over a period of seven days or more; and
    the pharmaceutical formulation comprises 50 mg to 500 mg of ciprofloxacin.

6. The method of claim 1 wherein:
    the aerosolizing and inhalation are repeated once each day to provide a daily dose over a period of seven days to fifty-six days; and
    wherein each daily dose comprises 75 mg to 300 mg of ciprofloxacin.

7. A method of treatment of an antibiotic resistant infection in a patient, comprising:
    aerosolizing a formulation to yield an aerosolized formulation comprising aeorosolized particles having an aerodynamic diameter in a range of from 1 micron to 12 microns;
    wherein the aerosolized formulation comprises:
        a liquid carrier comprising ciprofloxacin at a concentration of 20 mg/mL to 80 mg/mL in solution,
        liposomes comprising ciprofloxacin in solution encapsulated in the liposomes,
        and ciprofloxacin as nanocrystals encapsulated inside the liposomes; and
    providing the aerosolized formulation for inhalation of the aerosolized formulation into the patient's lungs whereby 90% or more of the liposomes maintain structural integrity after being aerosolized and after contacting lung tissue provide a ciprofloxacin release rate of 0.5% to 10% per hour,
    whereby an antibiotic resistant infection comprises microorganisms in a biofilm in the lung of the patient, and the liposomes release drug over a period of time and at a rate effective in treating the biofilm infection;
    wherein the formulation further comprises a cryopreservative and a surfactant and the liposomes have an average particle size of about 75 nm to about 120 nm and are unilamellar.

8. The method of treatment of claim 7, wherein the infection is an infection of microorganisms selected from the group consisting of *P. aeruginosa* and *F. tularensis*.

9. The method of treatment of claim 7, wherein:
    the liposomes further comprise cholesterol and hydrogenated soy phosphatidyl-choline (HSPC) at a ratio of about 30 to 70 (plus or minus 10%); and
    wherein the formulation further comprises an excipient suitable for pulmonary delivery comprised of sodium acetate and an isotonic buffer: and
    further wherein 90% or more of the liposomes maintain integrity when aerosolized.

10. The method of treatment of claim 7, wherein:
    95% or more of the liposomes maintain integrity when aerosolized and after contacting lung tissue provide a ciprofloxacin release rate of 1% to 8% per hour; and
    the liposomes are unilamellar and comprise cholesterol and hydrogenated soy phosphatidyl-choline (HSPC) at a ratio of such that 98% or more of the liposomes maintain integrity when aerosolized, and provide a ciprofloxacin release rate of 2% to 6% per hour.

11. The method of treatment of claim 7, wherein:
    the formulation further comprises 0.1 to 0.3% polysorbate 20, and 200 to 400 mg/mL sucrose,
    wherein the aerosolizing and inhaling are repeated once each day to provide a daily dose over a period of seven days or more; and
    wherein each daily dose comprises 50 mg to 500 mg of ciprofloxacin.

12. The method of treatment of claim 7, wherein:
the aerosolizing and inhalation are repeated once each day over a period of seven days to fifty-six days; and
wherein each daily dose comprises 75 mg to 300 mg of ciprofloxacin.

13. The method of treatment of claim 7, wherein,
the aerosolized particles have an aerodynamic diameter of two microns to eight microns, the liposomes have a diameter of less than 1 micron,
and nanocrystals in the liposome have a dimension of 100 nanometers; and
wherein the ciprofloxacin is present in the solution at a concentration of 40 mg/mL to 60 mg/mL;
and
further wherein the liposomes are unilamellar and maintain structural integrity at a level of 90% or more after aerosolizing.

14. The method of treatment of claim 7,
wherein the liposomes are characterized such that 95% or more of the liposomes maintain structural integrity and continue to encapsulate nanocrystals of ciprofloxacin in the aerosolized formulation.

15. The method of treatment of claim 7, wherein the liposomes are characterized such that 98% or more of the liposomes maintain structural integrity and continue to encapsulate nanocrystals of ciprofloxacin in the aerosolized formulation.

* * * * *